(12) United States Patent
Soluri et al.

(10) Patent No.: US 7,274,022 B2
(45) Date of Patent: Sep. 25, 2007

(54) SCINTIGRAPHIC DEVICE WITH VARIABLE RESOLUTION

(75) Inventors: Alessandro Soluri, Rome (IT); Marco Piano, Palmanova (IT); Raffaele Scafe, Anguillara Sabazia (IT); Francesco Scopinaro, Rome (IT)

(73) Assignee: CNR-Consiglio Nazionale Delle Ricerche, Rome (IT)

( * ) Notice: Subject to any disclaimer, the term of this patent is extended or adjusted under 35 U.S.C. 154(b) by 90 days.

(21) Appl. No.: 11/137,425

(22) Filed: May 26, 2005

(65) Prior Publication Data
US 2005/0263717 A1    Dec. 1, 2005

(30) Foreign Application Priority Data
May 31, 2004   (IT)   .................. RM2004A0271

(51) Int. Cl.
*G01T 1/164* (2006.01)
(52) U.S. Cl. .................................. 250/363.1
(58) Field of Classification Search ............. 250/363.1
See application file for complete search history.

(56) References Cited
U.S. PATENT DOCUMENTS

| | | | |
|---|---|---|---|
| 3,591,808 A * | 7/1971 | Prag et al. ................ | 250/368 |
| 3,882,314 A | 5/1975 | Benedetti et al. | |
| 4,118,632 A * | 10/1978 | Luig ........................ | 250/363.1 |
| 5,222,114 A | 6/1993 | Kamata et al. | |
| 6,734,430 B2 * | 5/2004 | Soluri et al. .............. | 250/363.1 |
| 2002/0175289 A1 | 11/2002 | Soluri et al. | |
| 2003/0136916 A1 | 7/2003 | Kearfott et al. | |

* cited by examiner

*Primary Examiner*—Constantine Hannaher
(74) *Attorney, Agent, or Firm*—Young & Thompson

(57) ABSTRACT

A scintigraphic device includes a case open at an application end, and coated by a shielding shell; a collimator positioned inside the case, made of a material with high atomic number and high density and having a plurality of collimation channels extending mutually parallel according to a predefined direction of measurement; a measuring member positioned inside the case in proximity to the collimator and including a scintillation crystal for converting each ionizing radiation originating from a source in exam into light radiation, and at least one photosensor, for determining the energy and the position of each detected event. The measuring member and the collimator are relatively movable to increase and/or reduce the distance between the converter and the application end and consequently to vary the total length of the collimator. The collimator may include two or more blocks at least one of which is movable relative to the others.

28 Claims, 17 Drawing Sheets

SCINTIGRAPHIC DEVICE WITH VARIABLE RESOLUTION

BACKGROUND OF THE INVENTION

The present invention relates to a scintigraphic device of the kind comprising: a case open at an application end and coated with a shielding shell; a collimator made of a material with high atomic number and high density and having a plurality of collimation channels extending substantially parallel to each other according to a predefined direction of measurement, the collimator being positioned inside the case in such a way as to allow the passage of radiation directed substantially parallel to the direction of measurement; a measuring member positioned inside the case in proximity to the collimator and comprising at least one converter able to convert each ionizing radiation coming from a source in exam in light radiation and at least one photosensor for determining the energy associated to each event and its position in the visual field; at least one electronic processing unit operatively associated to the photosensor.

The present invention is aimed at the diagnostic medical sector, and in particular, it is dedicated to the location of tumor lesions and similar pathologies or to the observation of radio marked substances, introduced into the organisms before the exam to be conducted in order to visualize the distribution of the introduced substance.

As is well known, the systems for locating and visualizing the distribution of radioactivity, such as those illustrated and described in the U.S. Pat. Nos. 6,242,744 B1 and U.S. Pat. No. 6,232,605 B1, operate on particularly small visual fields and are used in Nuclear Medicine as locating and diagnostic device able to identify neoplasias with high spatial resolution. It is also known that the aforementioned devices are used to carry out scintigraphic analyses on small animals, to test new radio-marked antibodies, specific for determined pathologies. It is also possible that said scintigraphic devices are used for the guided location of lesions of the prostate and of the breast, in order to identify the regions subjected to high capture to be subjected to bioptic sampling, integrating current radiographic and/or echographic techniques. These devices can also find additional applications in Astrophysics and in systems for industrial non destructive checks.

More specifically, the main use of the aforementioned device pertains to the location of tumor lesions, especially in those techniques that require an adequate precision in detection such as biopsies (prostate and breast) or in radio-guided or radio-immunoguided interventions during which the detected signals are converted in digital form to provide necessary information through light or sound scales related to the intensity of the signals that fall within the selected energy window.

Although known technologies allow quite precise diagnoses, the Applicant has noted that they are nonetheless not free of some drawbacks, mainly in relation to spatial resolution in general, and in particular, to the spatial resolution of about one centimeter, as well as to the dimensions and to the overall masses of the current gamma-cameras present on the market.

These problems, along with a growing and necessary demand for definition and spatial resolutions of the aforementioned diagnostic instruments and/or devices, have already been confronted in the U.S. Pat. Nos. 6,242,744 and U.S. Pat. No. 6,232,605 (Soluri et al.), U.S. Pat. No. 5,783,829 (Sealock et al.), U.S. Pat. No. 5,864,141 (Majewski et al.), U.S. Pat. No. 6,021,341 (Scibilia et al.) and in the international patent WO 96/37791 (De Notaristefani et al.). This notwithstanding, in some applications the required spatial resolutions is a fundamental parameter, so still higher resolutions must be obtained. The achievement of a high spatial resolutions, however, is hindered by inaccuracies in the location of one or more events detected by the scintillation crystals. This drawing persists even if to the crystal matrices are associated last generation photomultipliers, or photo tubes, known as PSPMT (Position Sensitive Photomultiplier Tube) and a high resolution lead collimator, generally provided with hexagonal holes. It is also detectable in the presence of scintillation crystals positioned inside the individual holes of the collimators or of planar elements positioned at the collimators, as described in U.S. Pat. No. 6,734,430 (Soluri et al.).

Another factor able negatively to influence the spatial resolution of the aforementioned diagnostic devices is the length of the respective collimators, unsuitable for the type of exam to be performed, as well as the distance of the lesions to be detected and located with respect to the scintillation crystals. In general, the difficulty in locating lesions increases as a function of their distance from the detector.

Usually, scintigraphic devices are provided with collimators with fixed length, chosen and mounted according to the type of exam or detection to be carried out. The collimators may also be replaced by other collimators with different structural characteristics. However, the complicated operation of replacing the collimators is rarely performed to execute particular exams that require a different spatial resolution or counting efficiency from those normally in use.

SUMMARY OF THE INVENTION

The main object of the present invention is to propose a scintigraphic device that enables to vary automatically, or with manual command, the overall length of the collimator in relation to the characteristics of the lesion to be examined (diameter, depth and lesion/bottom radioactivity concentration ratio), collimation length can be so regulated as to visualize the lesion with the best possible contrast, under given instrumental conditions. This operation can be completed without replacing the collimators.

In other words, the object is to obtain a device dedicated to an optimized imaging system, intended for single scintigraphic applications, optimizing the expected result by regulating collimator length automatically or manually.

Another object of the present invention is to provide a scintigraphic device with reduced dimensions and limited masses, usable also for external diagnoses of small tumors, e.g. skin melanomas, thyroid pathologies and so on, easy to handle and able to visualize areas of interest that are difficult to reach with current devices.

These objects and others besides, which shall become more readily apparent in the course of the present description are achieved by a scintigraphic device comprising the characteristics expressed in one or more of the claims that follow.

BRIEF DESCRIPTION OF THE DRAWINGS

Further characteristics and advantages shall become more readily apparent from the detailed description of a preferred, but not exclusive embodiment of a scintigraphic device according to the present invention. Said description shall be set out hereafter with reference to the accompanying draw ings, provided purely by way of non limiting indication, in which.

DESCRIPTION OF THE PREFERRED EMBODIMENTS

Figure 1:
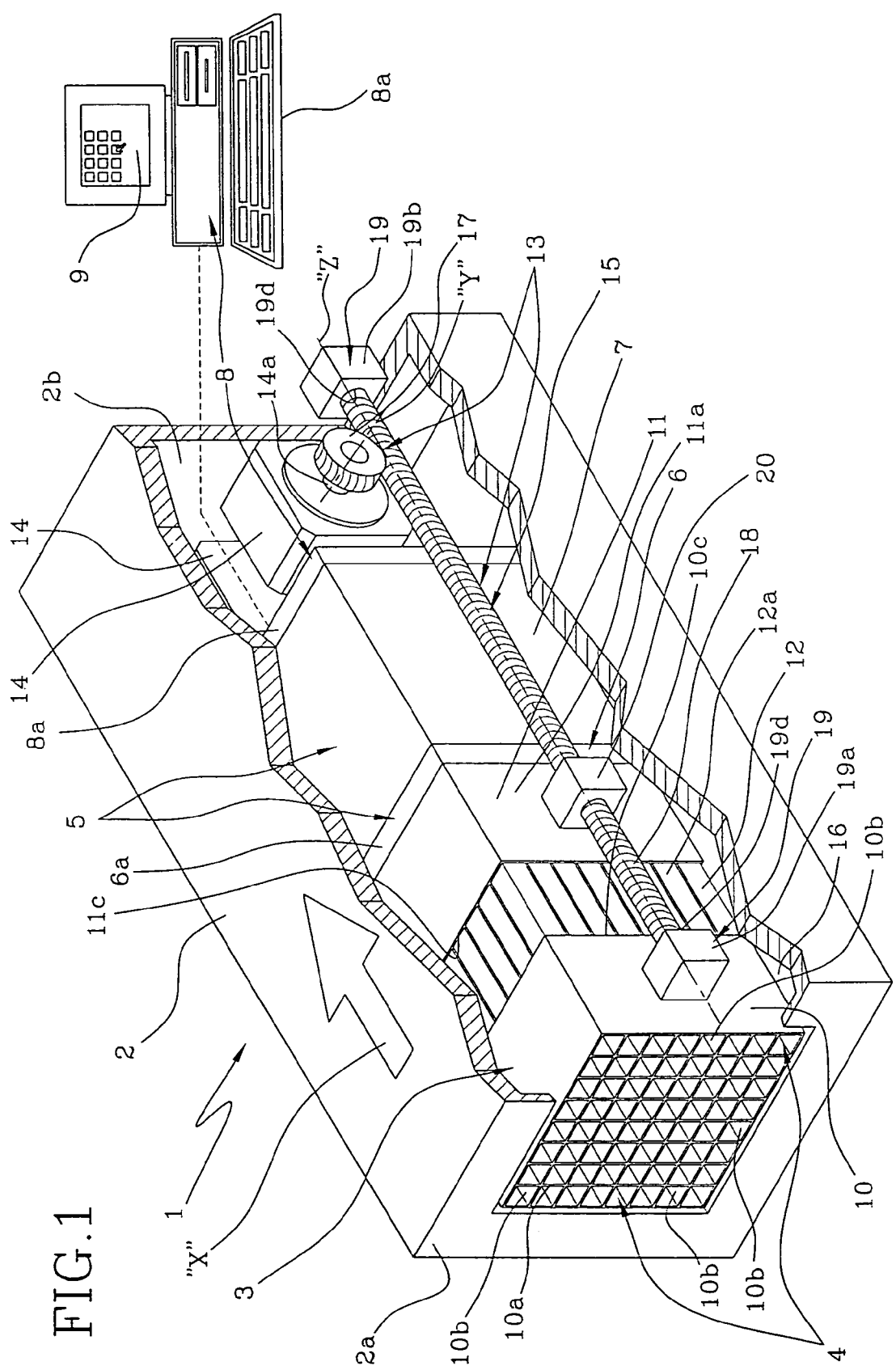
FIG. 1 is a partially interrupted perspective view of a scintigraphic device in accordance with a first embodiment of the present invention.

With reference to the accompanying figures, the number 1 globally designates a scintigraphic device in accordance with the present invention.

As shown in the accompanying figures, the scintigraphic device 1 comprises a case 2 open at an application end 2a and coated by a shielding shell. Inside the case 2 is positioned a collimator 3 made of a material with high effective atomic number ($Z_{eff}$) and high density, such as tungsten, platinum, lead, gold, tantalum, palladium, and so on, in pure form or alloyed. Such material is provided with high power of attenuation of the intensity of the radiation (of fixed or lower energy) originating from regions of the visible range not included in the solid angle intercepted by the collimator. In detail, the collimator 3 has a plurality of collimation channels 4 extending substantially parallel to each other and to a predefined direction of measurement "X", substantially perpendicular to an external surface of the source subjected to examination.

Again with reference to the accompanying figures, the device 1 further comprises at least one measuring member 5 positioned inside the case 2 in proximity to the collimator 3. The measuring member 5 comprises at least one converter 6 able to convert each ionizing radiation coming from a source in exam into light radiation and at least one photosensor 7 able to convert the light radiation coming from the converter 6 into corresponding electrical signals. Alternatively, it is also possible to use as a photosensor 7 a photo tube device, a diode or photodiode device or similar semiconductor systems.

Advantageously, the photosensor 7 is of the kind with anodes or crossed wires adapted to receive the light radiation coming from the converter 6 and to generate electrical signals necessary to measure the energy released in the individual scintillation event and to determine the position co-ordinates.

Preferably, the photosensors 7, photomultipliers or photo tubes or photodiodes, constituting the measuring member 5 together with the scintillation crystals of the device 1, are last generation, known as PSPMT (Position Sensitive Photomultiplier Tube), while the converter 6 is constituted by matrices 6a of scintillation crystals (FIGS. 1-16) located between the collimator 3 and the photosensor 7. The converter 6 may also comprise a plurality of scintillation crystals 6b (FIGS. 15-16) operative internally to the collimator 3 or one or more planar elements (not shown because they are known) positioned between the collimator 3 and the photosensor 7.

Figure 15:
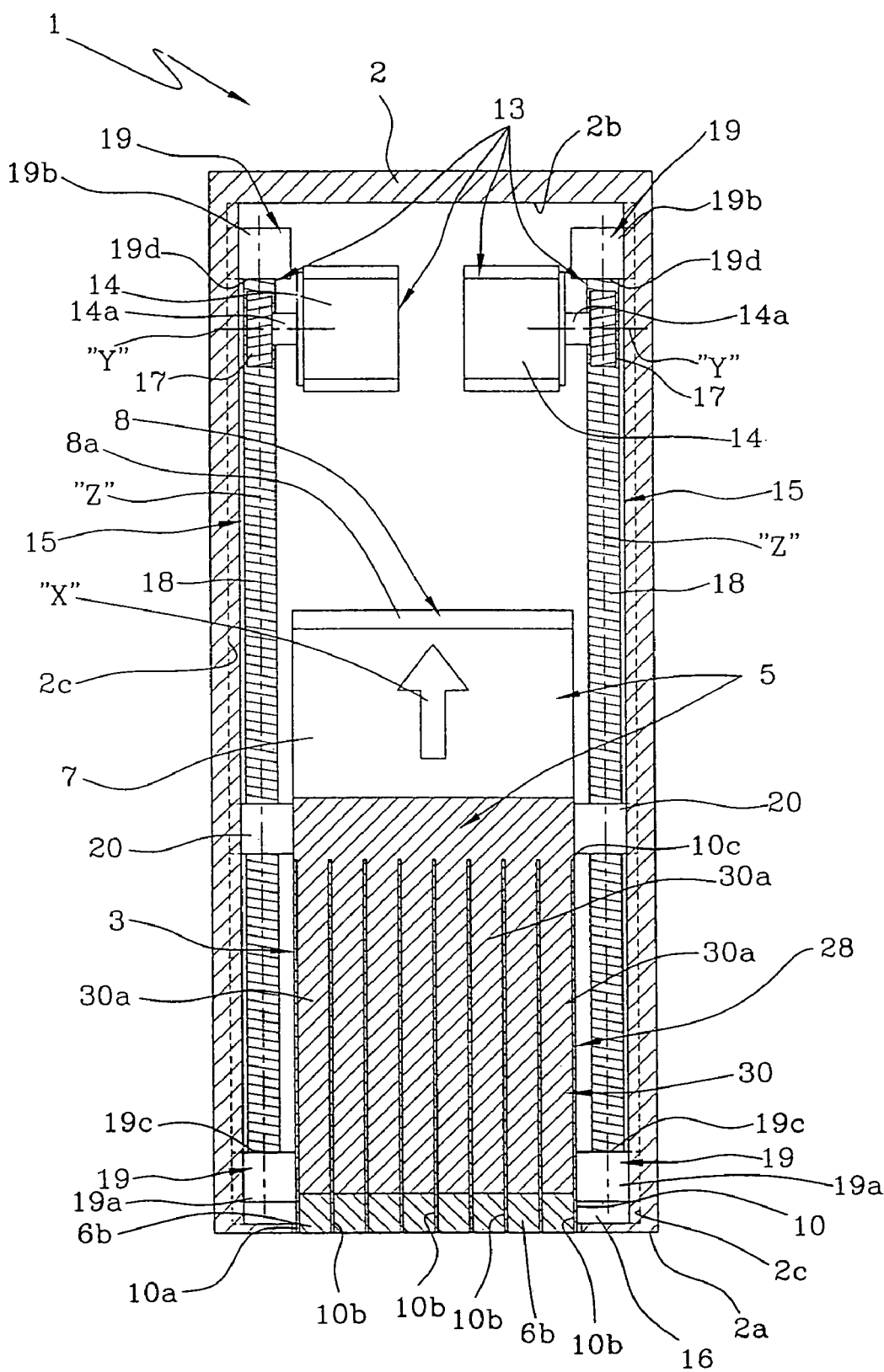
FIG. 15 is a plan section of the device of the previous figure, shown in a first operative position.
Figure 16:
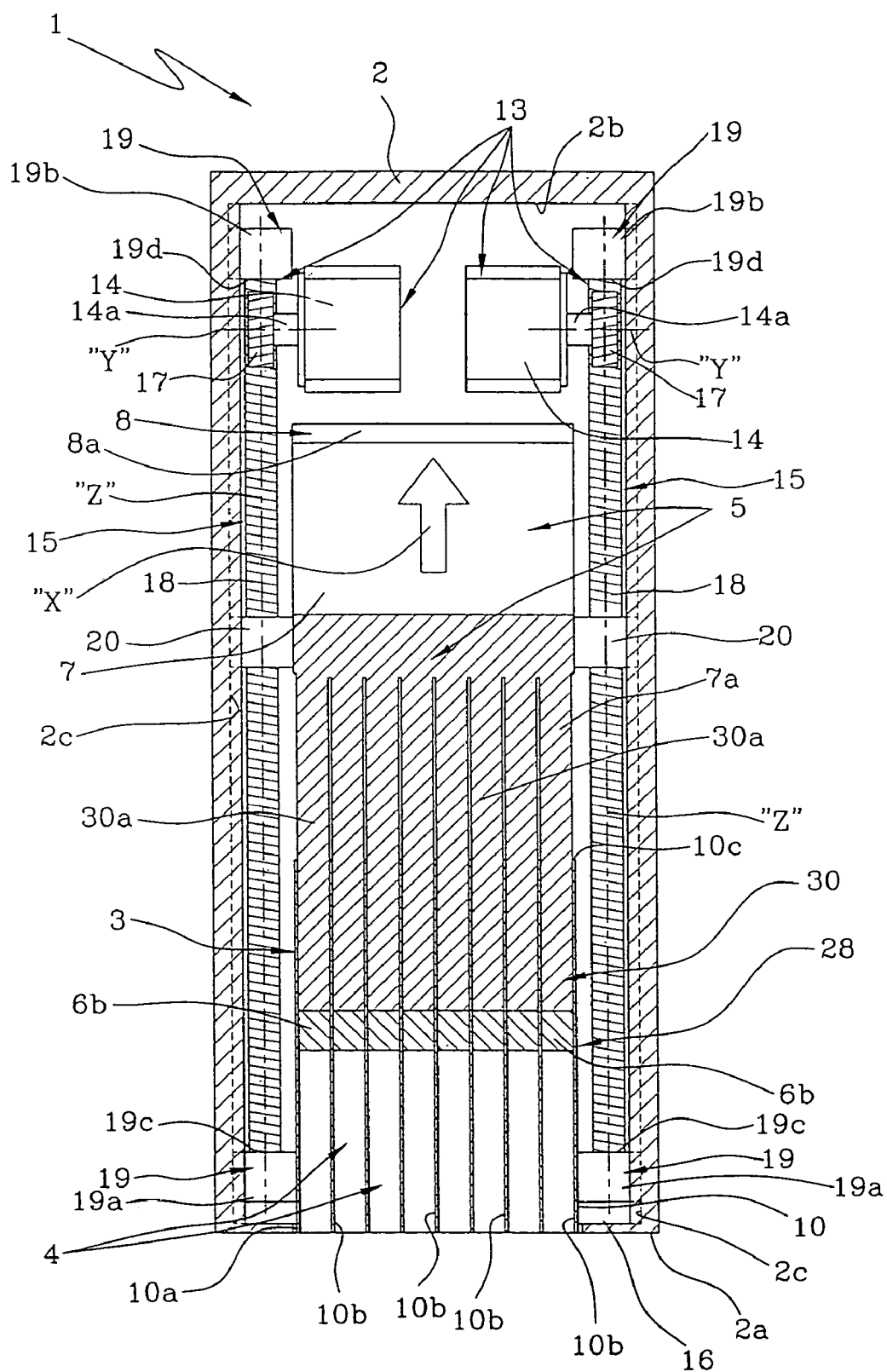
FIG. 16 is a plan section of the device of FIGS. 14 and 15 shown in a second operative position.

As shown in FIGS. 15 and 16, the scintillation crystals 6b have a substantially polyhedral, preferably cubic or parallelepiped, of appropriate thickness. The scintillation crystals 6b can be inorganic or organic, both at the hyper-pure state, and doped with suitable quantities of appropriate materials to enhance their scintillation properties (e.g.: CsI(Tl), CsI(Na), NaI(Tl)), according to the type of detection to be achieved, the diagnostic techniques and the tracers used. In any case, the emission spectrum of the scintillation light must have a good superposition with that of absorption of the photosensitive layer of the photosensor 7.

The photosensor 7 is connected to at least one electronic processing unit 8 positioned substantially at the opposite side relative to the application end 2a of the case 2. The electronic processing unit 8 is adapted to receive the electrical signals amplified and integrated by appropriate electronic components 8a associated to the photosensor 7, and to display, on an appropriate monitor 9 (FIGS. 1, 4, 7, 8, 11 and 14), a map representing the radioactivity distribution present within the body being examined at the region intercepted by the visual field.

Figure 2:
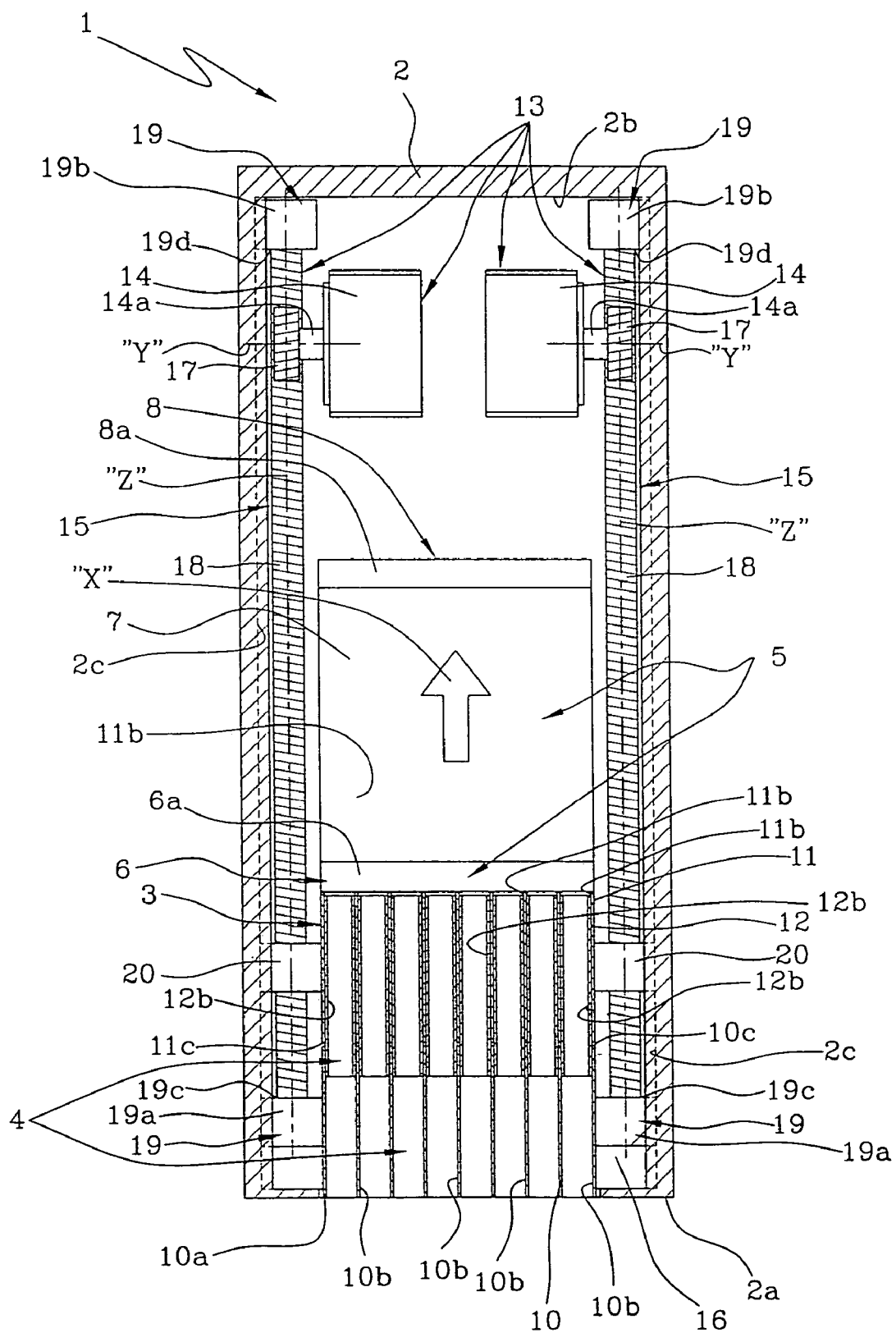
FIG. 2 is a plan section of the device of the previous figure, shown in a first operative position.
Figure 3:
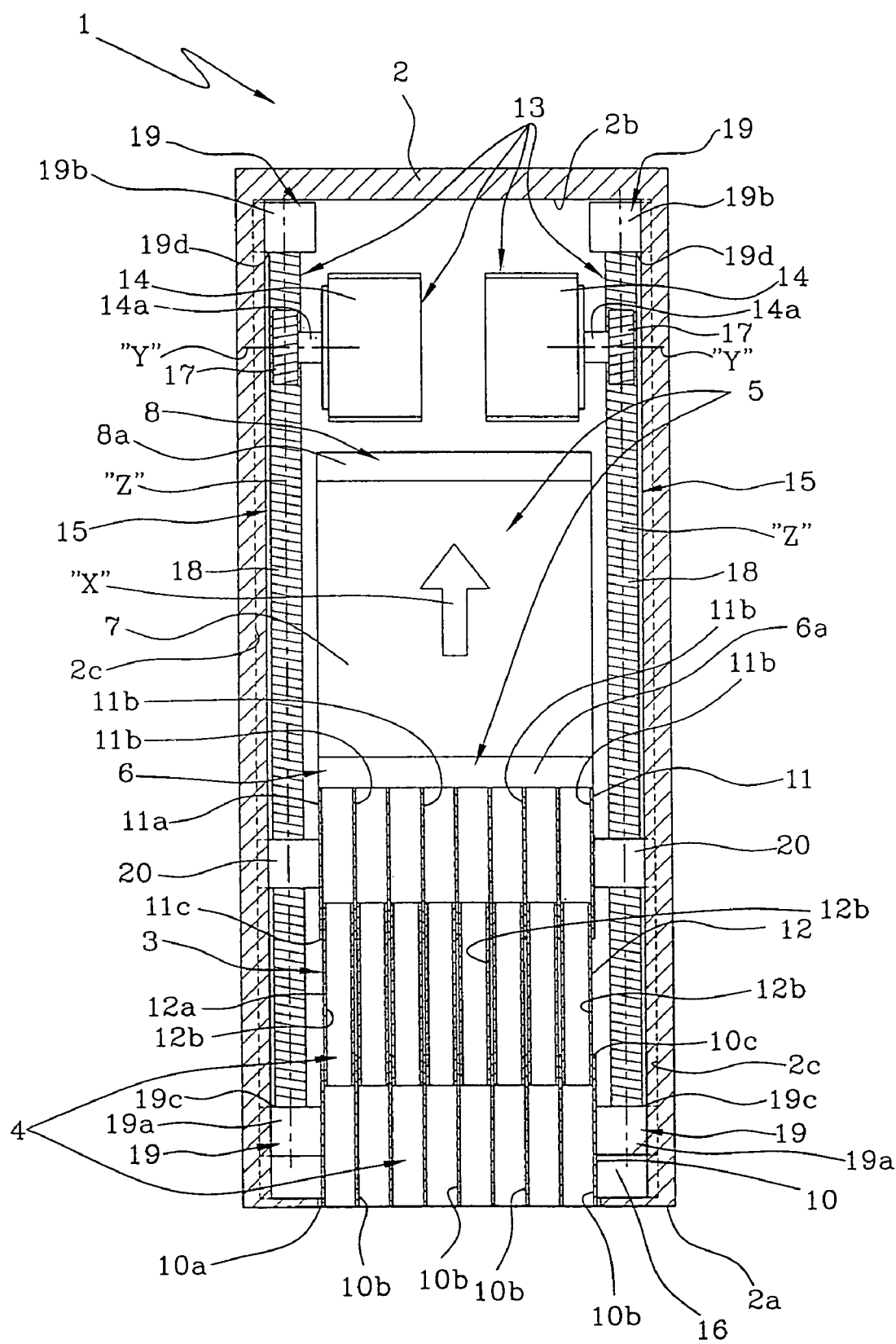
FIG. 3 is a plan section of the device of the previous figures shown in a second operative position.

In accordance with a first embodiment of the present invention, shown in FIGS. 1-3, the collimator 3 comprises at least one application block 10 having a structure 10a with parallelepiped shape, conformed substantially as a square matrix and positioned at the application end 2a of the case 2 according to a fixed position. In detail, the square matrix structure 10a of the application block 10 is defined by a plurality of collimation conduits 10b developing substantially parallel relative to the direction of measurement "X".

The collimator 3 further comprises at least one inner block 11 positioned at the measuring member 5 and at least one intermediate block 12 positioned between the application block 10 and the inner block 11. Both the inner block 11 and the intermediate block 12 have each a structure 11a with parallelepiped shape, conformed substantially as a square matrix and provided with a plurality of collimation conduits 11b, 12b extending substantially parallel relative to the direction of measurement "X". In particular, the collimation conduits 11b of the inner block are aligned to respective collimation conduits 10b of the application block 10 and to respective collimation conduits 12b of the intermediate block in such a way as to define the aforementioned collimation channels 4. The intermediate block 12 is integrally engaged to the application block 10 at the opposite side relative to the application end 2a of the case 2 and the inner block 11 is integrally engaged to the measuring member 5 at the converter 6 thereof.

As shown in FIGS. 2 and 3, each of the collimation conduits 12b of the intermediate block 12 has different transverse dimensions with respect to the transverse dimensions of the collimation conduits 10b, 11b of the application block 10 and of the inner block 11. More specifically, each of the collimation conduits 12b of the intermediate block 12 has smaller maximum transverse dimensions than the minimum transverse dimensions of the respective collimation conduits 11b at least of the inner block 11.

Advantageously, the inner block 11 is movable together with the measuring member 5 along the direction of measurement "X", between a first position, in which the converter 6 of the measuring member 5 is situated in proximity to the application end 2a of the case 2 (FIG. 2) and the intermediate block 12 is at least partially inserted in the inner block 11, and a second position, in which the converter 6 of the measuring member 5 is situated at a distant position relative to the application end 2a of the case 2 (FIG. 3) and the intermediate block 12 is positioned at a terminal edge 11c of the inner block 11, lying on a substantially perpendicular plane relative to the direction of measurement "X" and oriented towards the application end 2a. In other words, the inner block 11 is free to slide telescopically on the intermediate block 12 along the direction of measurement "X" and according to the entire longitudinal extension of the intermediate block 12 to reduce and/or increase the overall length of the collimator 4. Naturally, the measuring member 5 also moves integrally with the inner block 11 to reduce and/or increase the distance between the converter 6 and the application end 2a of the case 2.

By way of example, without thereby limiting the general nature of this description, the application block 10, the inner block 11 and the intermediate block 12 may have the same length, measured parallel to the direction of measurement "X", ranging between 4 mm and 100 mm, and preferably equal to 12 mm.

The device 1 comprises at least one actuation member 13 operatively associated to the case 2 to determine the relative actuation between the collimator 3 and the measuring member 5. The actuation member 13 comprises at least one main electrical motor 14, preferably of the stepping motor type, able to cause small displacements of the respective block 11 to be actuated and positioned within the case 2. In particular, the main electric motor 14 is situation in proximity to the measuring member 5 at the opposite site at the application end 2a.

The actuation element 13 further comprises transmission means 15 operatively interposed between the main electric motor 14 and at least the measuring member 5 to actuate the latter between the first and the second position. The transmission means 15 develop, longitudinally, between the main electric motor 14 and the collimator 3 and, transversely, between the case 2 and the measuring member 5, inside a transverse gap 16 of about 3-5 mm, preferably not exceeding 8 mm.

In detail, the transmission means 15 comprise at least one gear wheel 17 with helical teeth keyed on a drive shaft 14a projecting from the main electric motor 14. The gear wheel 17 can be actuated in rotation, together with the drive shaft 14a, around an axis of rotation "Y" that is substantially perpendicular to the direction of measurement "X". The transmission means 15 further comprise at least one worm screw 18 developing substantially parallel relative to the direction of measurement "X", from the gear wheel 17 to the application end 2a of the case 2. The worm screw 18 is meshed by the gear wheel 17 to be actuated in rotation around its own longitudinal axis "Z" as a result of the activation of the main electric motor 14.

The transmission means 15 also comprise support means 19 engaging the worm screw 18 by means of appropriate coupling systems (not shown because they are known) which allow only its rotation around its own longitudinal axis "Z". In other words, the support means 19 are adapted to support the worm screw 18 in such a way as to inhibit any horizontal and/or vertical translation induced on it by the action of the gear wheel 17 and to allow the rotation around its longitudinal axis "Z". Preferably, the support means 19 comprises a first support element 19a positioned at the application end 2a of the case 2 between the latter and the application block 10 of the collimator 3 and a second support element 19b positioned between the gear wheel 14 and a bottom 2b of the case 2. Both the first and the second support element 19a, 19b have at least one central engagement seat 19c, 19d for the rotary engagement of the worm screw 18. The first support element 19a is fastened both to the application block 10 of the collimator 3 and to the case 2 at a longitudinal seat 2c thereof, shaped complementarily both to the first and to the second support element 19a, 19b, while the second support element 19b is fastened only to the longitudinal seat 2c of the case 2.

The transmission means 15 are also provided with at least one actuating cursor 20 operatively engaged to the worm screw 18 at the opposite side with respect to the gear wheel 17 to translate thereof along a direction that is substantially parallel to the direction of measurement "X". The actuating cursor 20 is fastened externally to the inner block 11 of the collimator 3 and it is slidably engaged to the longitudinal guide 2c at the opposite side from the collimator 3 to drive the inner block 11 between the first and the second position.

With reference to the embodiment illustrated in FIGS. 1-3, the actuating member 13 is preferably provided with two main electric motors 14 and respective transmission means 15 operatively positioned at opposite parts with respect to the collimator 3. In this situation, the components described above are doubled, considerably increasing the stability of the moving marts.

Advantageously, the actuating member 13 is managed directly by the processing unit 8 which activates it automatically to adapt, by the sliding of the inner block 11 on the intermediate block 12 and the displacement of the measuring member 5 along the direction of measurement "X", the device 1 at each exam to be performed. In particular, the electronic processing unit 8 employs an appropriate software which, according to the function of the lesion/background ratio measured on the image, determines the positioning of the inner block 11 between the first (FIG. 2) and the second position (FIG. 3), i.e. respectively, a position of minimum length of the collimator 3 equal to the sum of the lengths of the application block 10 and inner block 11, between 8 mm and 120 mm, and preferably equal to 24 mm, or, a position of maximum length of the collimator 3 determined by the summation of the total lengths of each block 10, 11, 12, between 12 mm and 60 mm, preferably equal to 36 mm.

Naturally, the inner block 11 can also be placed according to any one of the intermediate positions to the first and to the second position. In this situation, the total length of the collimator 3 is obtained through the summation of the lengths of the application block 10, of the inner block 11 and of the intermediate block portion 12 not covered by the inner block 11.

Both for the first embodiment and for the subsequent solutions, the main electric motors 14 and/or the actuating member 13 tasked with actuating the detection organ 5 and/or one or more blocks 10, 11, 12 of the collimator 6, can also be positioned outside the case 2 having different structural characteristics and movable components from those described.

In accordance with a second embodiment of the present invention illustrated in FIGS. 4-7, the intermediate 12 of the collimator 3 is operatively engaged to the application block 10 at the opposite part with respective to the application end 2a of the case 2 and it is movable between a first position (FIG. 5), in which it is at least partially inserted inside the application block 10, and a second position (FIG. 6), in which the intermediate block 12 is positioned at a terminal edge 10c of the application block 10, lying on a plane that is substantially perpendicular to the direction of measurement "X" and oriented at the inner block 11. The actuation of the intermediate block 12, relative to the application block 10, is possible because of the difference of the transverse dimensions between the collimation conduits 10b of the application block 10 and the application conduits 12b of the intermediate block 12. In particular, in order to assure a relative sliding between the application block 10 and the intermediate block 12, each of the collimation conduits 12b thereof has smaller maximum transverse dimensions than the minimum transverse dimensions of the respective collimation conduits 10b of the application block 10.

In this case, each block 10, 11, 12 has a substantially parallelepiped shape, whose length, measured parallel to the direction of measurement "X" is between 4 mm and 100 mm, and, preferably, equal to 12 mm for the application block 10 and inner block 11, and equal to 24 mm for the intermediate block 12.

Figure 4:
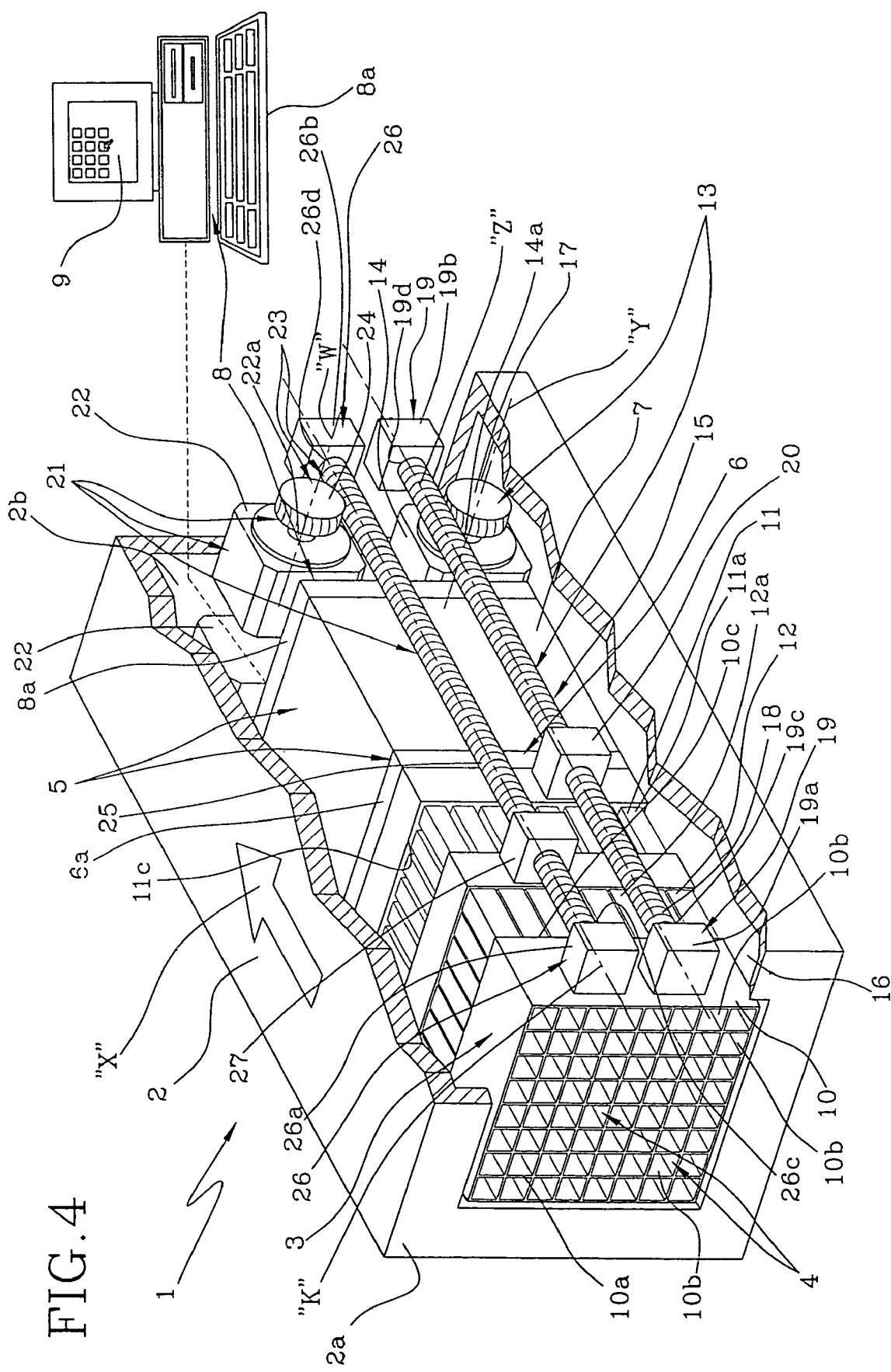
FIG. 4 is a partially interrupted perspective view of the scintigraphic device in accordance with a second embodiment of the present invention.
Figure 5:
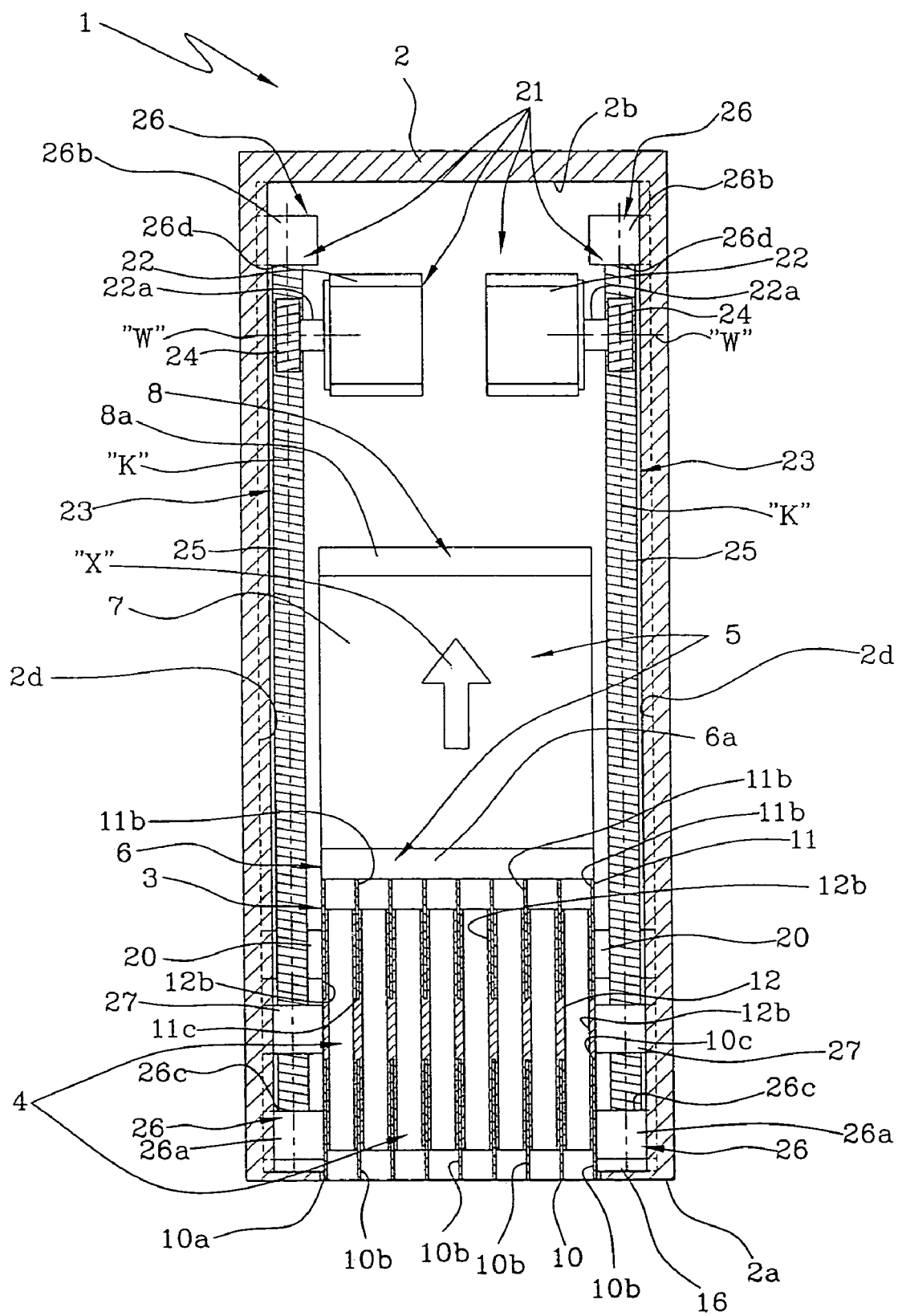
FIG. 5 is a plan section of the device of the previous figure, shown in a first operative position.
Figure 6:
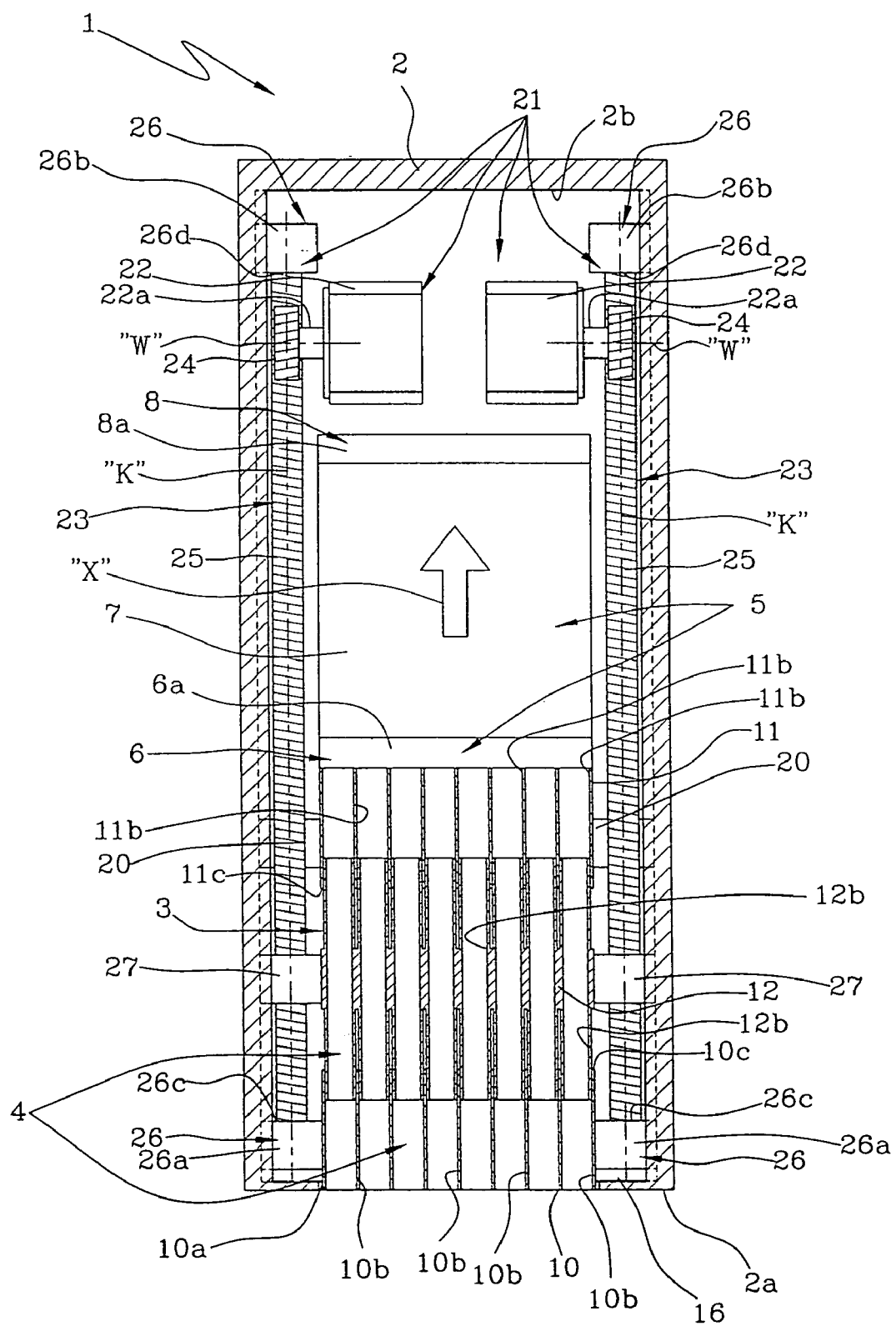
FIG. 6 is a plan section of the device of FIGS. 4 and 5 shown in a second operative position.
Figure 7:
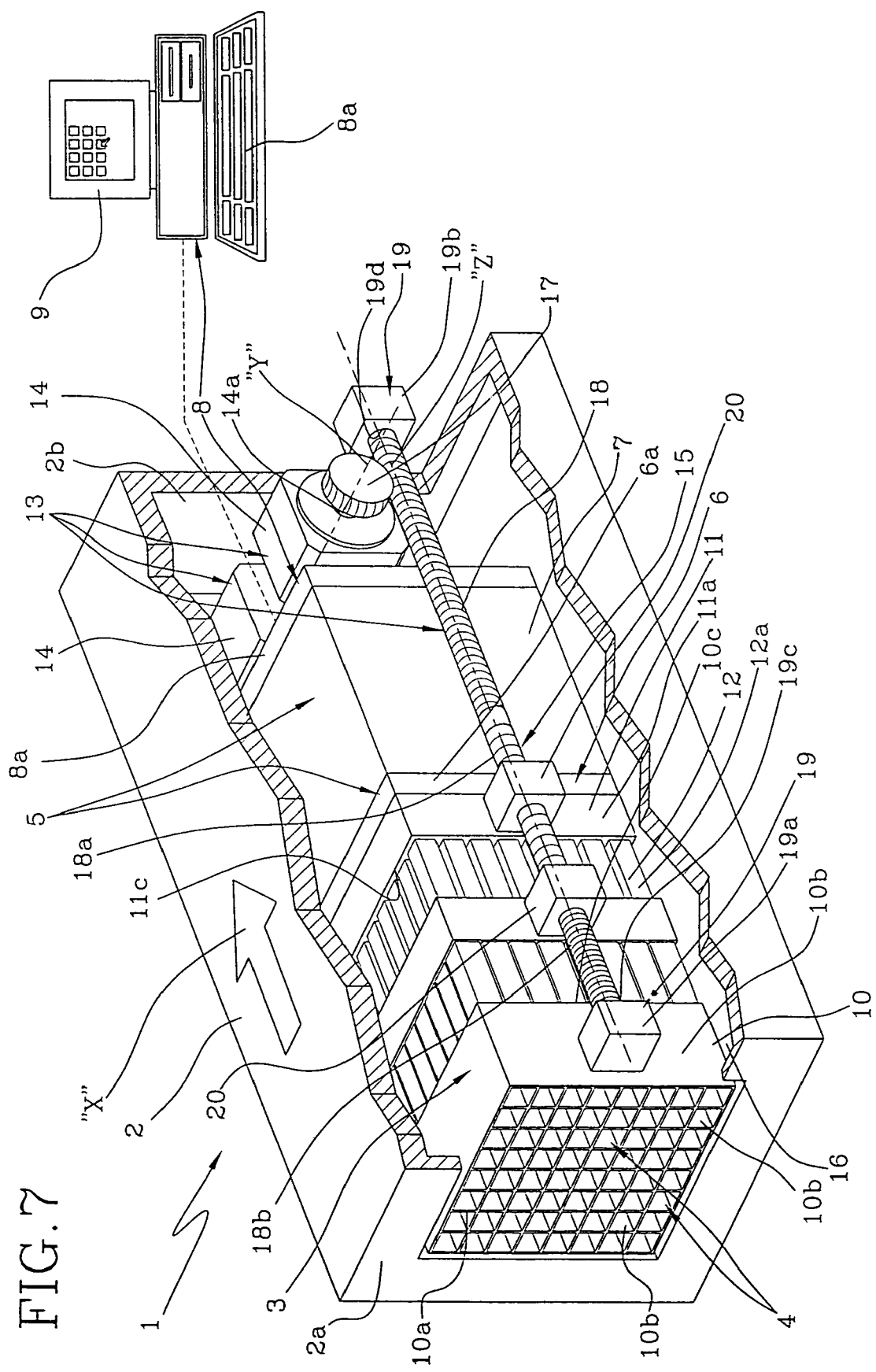
FIG. 7 is an additional perspective view of the device of FIG. 4 shown with different actuating members.

With reference to FIGS. 4-6, the actuating member 13 shown in the second embodiment differs from the actuating member 13 illustrated in the first one, due to the presence of an auxiliary actuating member 21 operatively interposed between the collimator 3 and the case 2 able to actuate the intermediate block 12 between the first and the second position.

Preferably, the auxiliary actuating member 21 comprises for each side of the collimator 3, an auxiliary electric motor 22 and respective transmission auxiliary means 23 operatively interposed between the auxiliary electric motor 22 and the intermediate block 12 of the collimator 3. In detail, the auxiliary transmission means 23 comprise at least one auxiliary gear wheel 24 with helical teeth keyed on an auxiliary drive shaft 22a projecting from the respective auxiliary electric motor 22. The auxiliary gear wheel 24 rotates integrally with the auxiliary drive shaft 22a around an axis of rotation "W" substantially perpendicularly to the direction of measurement "X" when the respective auxiliary electric motor 22 is activated. The auxiliary transmission means 23, present at each side 3a of the collimator 3, further comprise at least one auxiliary worm screw 25 developing substantially parallel to the direction of measurement "X", above the corresponding worm screw 18 of the actuating member 13. The auxiliary worm screw 25 is meshed by the respective auxiliary gear wheel 24 to be actuated in rotation thereby around its own longitudinal axis "K".

The auxiliary actuation member 21 too is provided with auxiliary support means 26 engaging the auxiliary worm screws 25 to support them between the measuring member 5 and the case 2. More specifically, the support auxiliary means 26 constrain the respective auxiliary worm screws 25 in such a way that the latter are only free to rotate around its own longitudinal axis "K".

As shown in FIGS. 4-6 the auxiliary support means 26 comprise, for each auxiliary worm screw 25, a first and second auxiliary support element 26a, 26b. The first auxiliary support element 26a is preferably positioned at the application end 2a of the case 2 between it and the application block 10 of the collimator 3, while the second auxiliary support element 26b is situated on an inner end 25a of the respective worm screw 25, at the opposite part relative to the first auxiliary support element 26a. The first support element 26a is fastened both to the application block 10 of the collimator 3 and to a respective auxiliary seat 2d obtained internally to the case 2 superiorly to the longitudinal seat 2c. The second support element 26b instead is fastened only to the auxiliary seat 2d.

As shown in FIGS. 4-6, each auxiliary support element 26a, 26b has a respective central engagement seat 26c, 26d for the rotary engagement of the respective auxiliary worm screw 25. Preferably, the auxiliary seat 2d of the case 2 is shaped complementarily to the auxiliary support elements 26a, 26b of the auxiliary transmission means 23.

The auxiliary transmission means 23 are also provided, for each auxiliary worm screw 25, with at least one auxiliary actuating cursor 27. Each auxiliary actuating cursor 27 is fastened to the intermediate block 12 of the collimator 3 and is slidably engaged to the auxiliary seat 2d of the case 2 to drive the intermediate block 12 between the first and the second position translating on the respective auxiliary worm screw 25 along the direction of measurement "X".

Alternatively, the relative actuation between the blocks 10, 11, 12 of the collimator 3 can also be embodied, as showed in the variant of the second embodiment (FIG. 7), by a single actuating member 13. In this situation, the worm screws 18 of the respective transmission means 15 have two consecutive 18a, 18b, with differentiated pitch, operatively engaged respectively by an actuating cursor 20 and an auxiliary actuating cursor 27. In this case, the actuating cursors 20, 27 translate on the respective worm screw 18 along a direction that is substantially parallel to the direction of measurement "X" according to the different speed of advance. The actuating cursor 20 is fastened externally to the inner block 11 of the collimator 3 to move it together with the measuring member 5 between the first and the second position and the auxiliary actuating cursor 27 is fastened externally to the intermediate block 12 to drive it between the first and second position as a result of the operation of the respective main electric motor 14.

With reference to the FIGS. 4-7, the collimator 3 can thus be elongated and shortened along a direction parallel to the direction of measurement "X" through the actuation of the intermediate block 12 and inner block 11, on the command of the electronic processing unit 8 between a minimum length (FIG. 5), determined by the summation of the lengths of the application block 10 and internal block 11, preferably equal to 24 mm, and a maximum length (FIG. 6), determined by the summation of the lengths of all blocks 10, 11, 12, preferably equal to 48 mm.

In particular, the collimator 3 is in condition of minimum length (FIG. 5) when the intermediate block 12 is in a first position, i.e., completely inserted inside the application block 10, and the inner block 11 has the measuring member 5, in first position, i.e., completely superposed to the intermediate block 12 against the application block 10. Vice versa, the collimator 3 is in condition of maximum length (FIG. 6) when the intermediate block 12 is in second position, i.e. almost completely extracted from the application block 10, and the inner block 11, together with the measuring member 5 is situated in the second position, i.e. almost totally extracted from the intermediate block 12.

The collimator 3 can also assume, depending on diagnostic requirements, any other length between the minimum and the maximum one. In this case, total length is determined by the visible part of the collimator 3, defined by the summation of the length of the application block 10, of the inner block 11 and of the exposed portion of the intermediate block 12.

Figure 8:
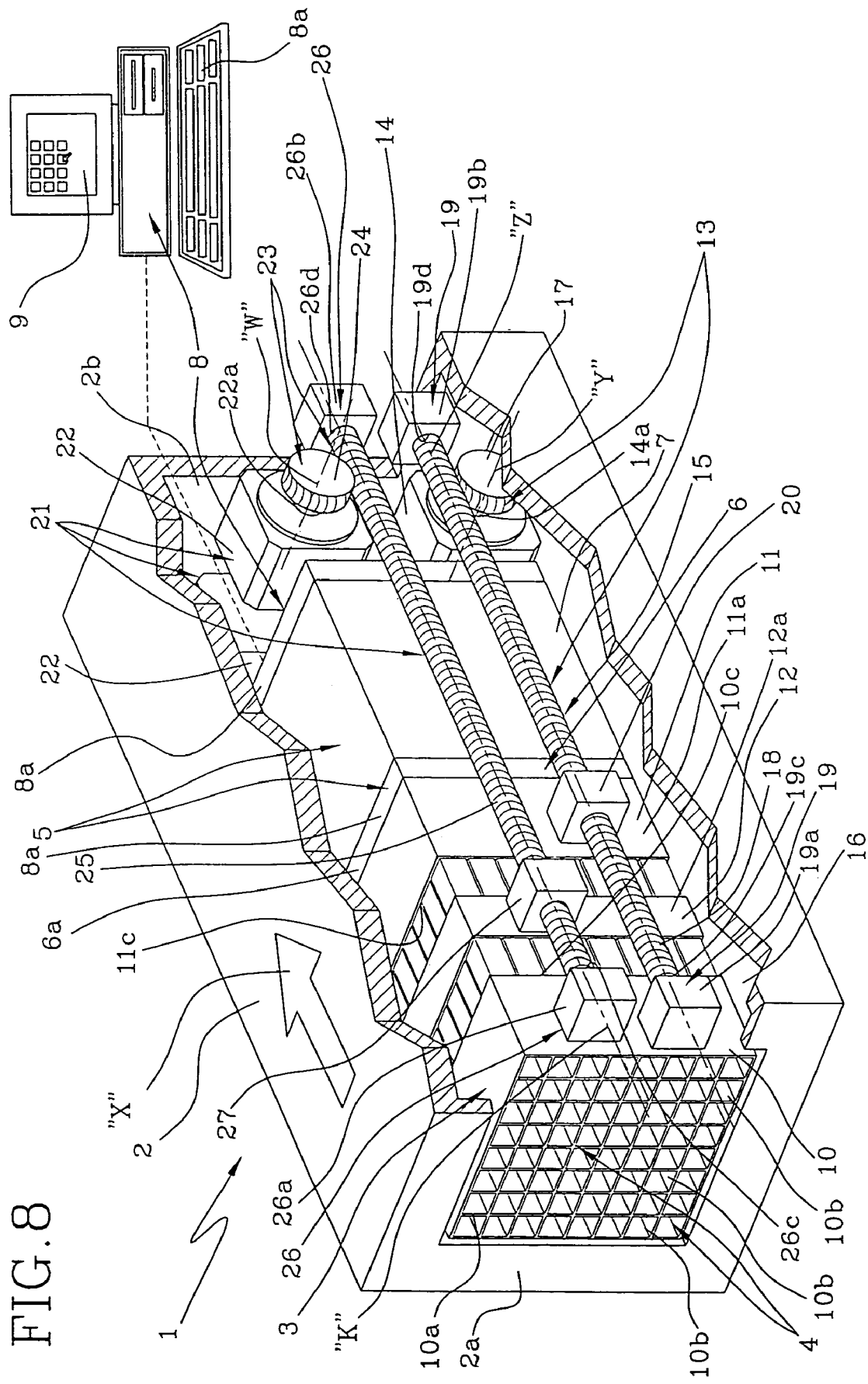
FIG. 8 is a partially interrupted perspective view of the device in accordance with a third embodiment of the present invention.
Figure 9:
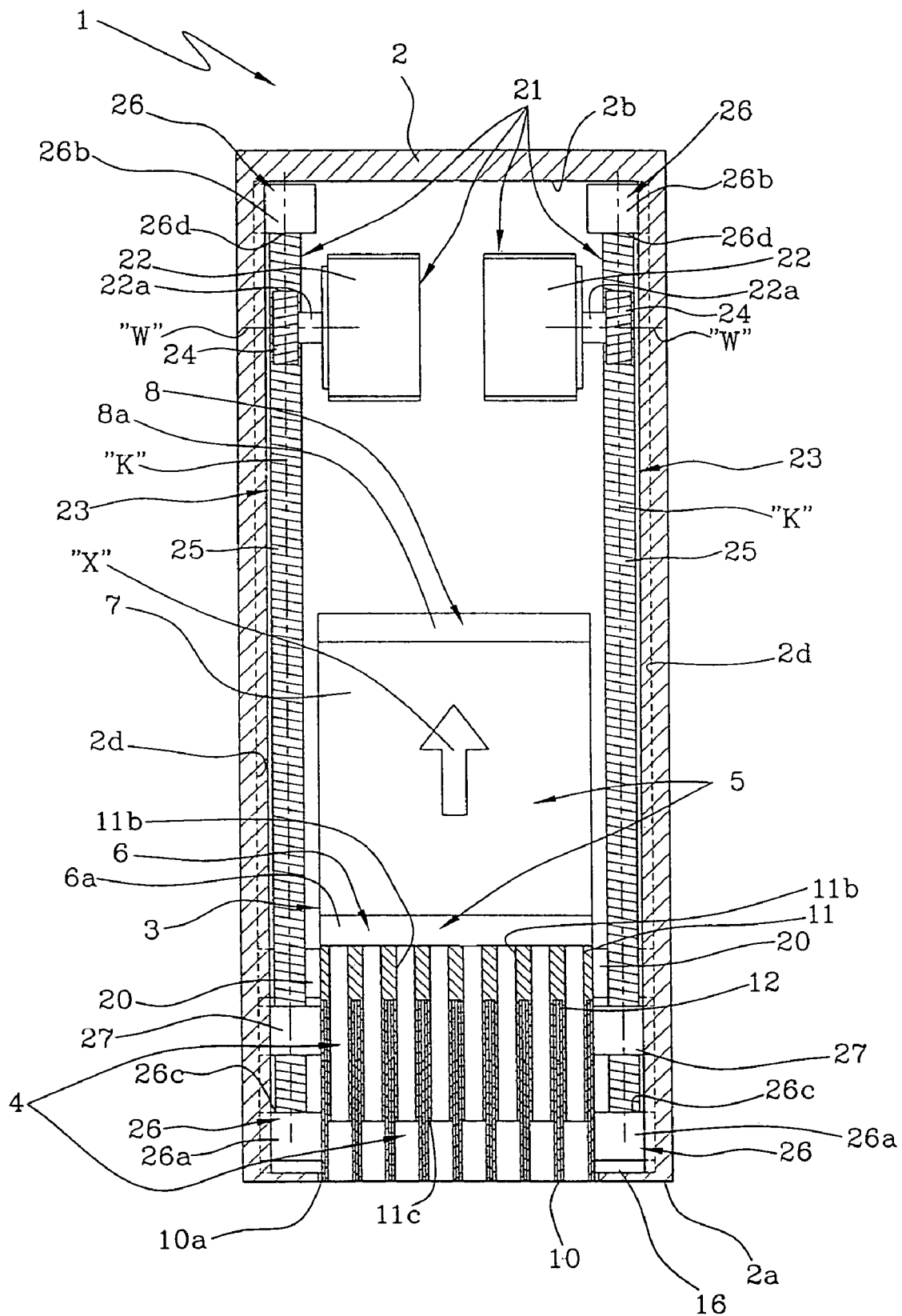
FIG. 9 is a plan section of the device of the previous figure, shown in a first operative position.
Figure 10:
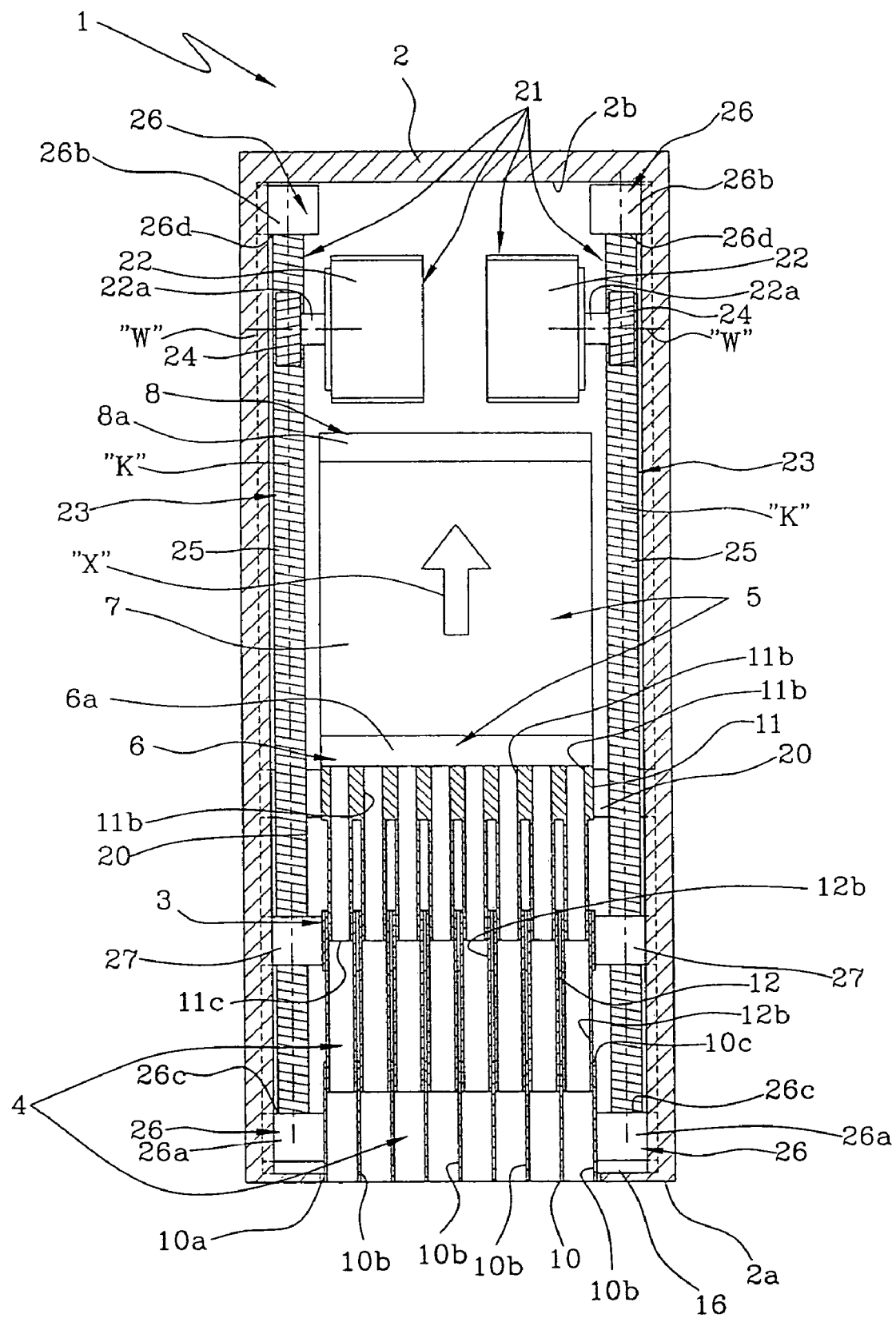
FIG. 10 is a plan section of the device of FIGS. 8 and 9 shown in a second operative position.

In accordance with a third embodiment of the present invention illustrated in FIGS. 8-10, each of the collimation conduits 12b of the intermediate block 12 has smaller maximum transverse dimensions than the minimum transverse dimensions of the respective collimation conduits 10b of the application block 10 and greater minimum transverse dimensions than the maximum transverse dimensions of the respective collimation conduits 11b of the inner block 11. In other words, the cross section of the collimator 3 becomes progressively smaller moving away from the application end 2a of the case 2.

Contrary to the second embodiment, the inner block 11 of the collimator 3 is free to slide together with the detection with the measuring member 5 inside the intermediate block 12 between the first position (FIG. 9) and the second position (FIG. 10).

As shown in FIGS. 8-10, the relative movement between the blocks 10, 11, 12 of the collimator 3 and the measuring member 5 can be embodied in similar fashion to the second embodiment, i.e., by means of an actuating member 13 and an auxiliary actuating member 23, or by means of a single actuating member 13 provided with worm screws 18 having portions 18a, 18b with differentiated pitch.

The parameters relating to the lengths of the respective blocks 10, 11, 12 measured parallel to the direction of measurement "X", as well as to the length of the length of the collimator 3 in any operative condition, are substantially similar to the parameters previously provided in relation to the first and to the second embodiment.

Figure 11:
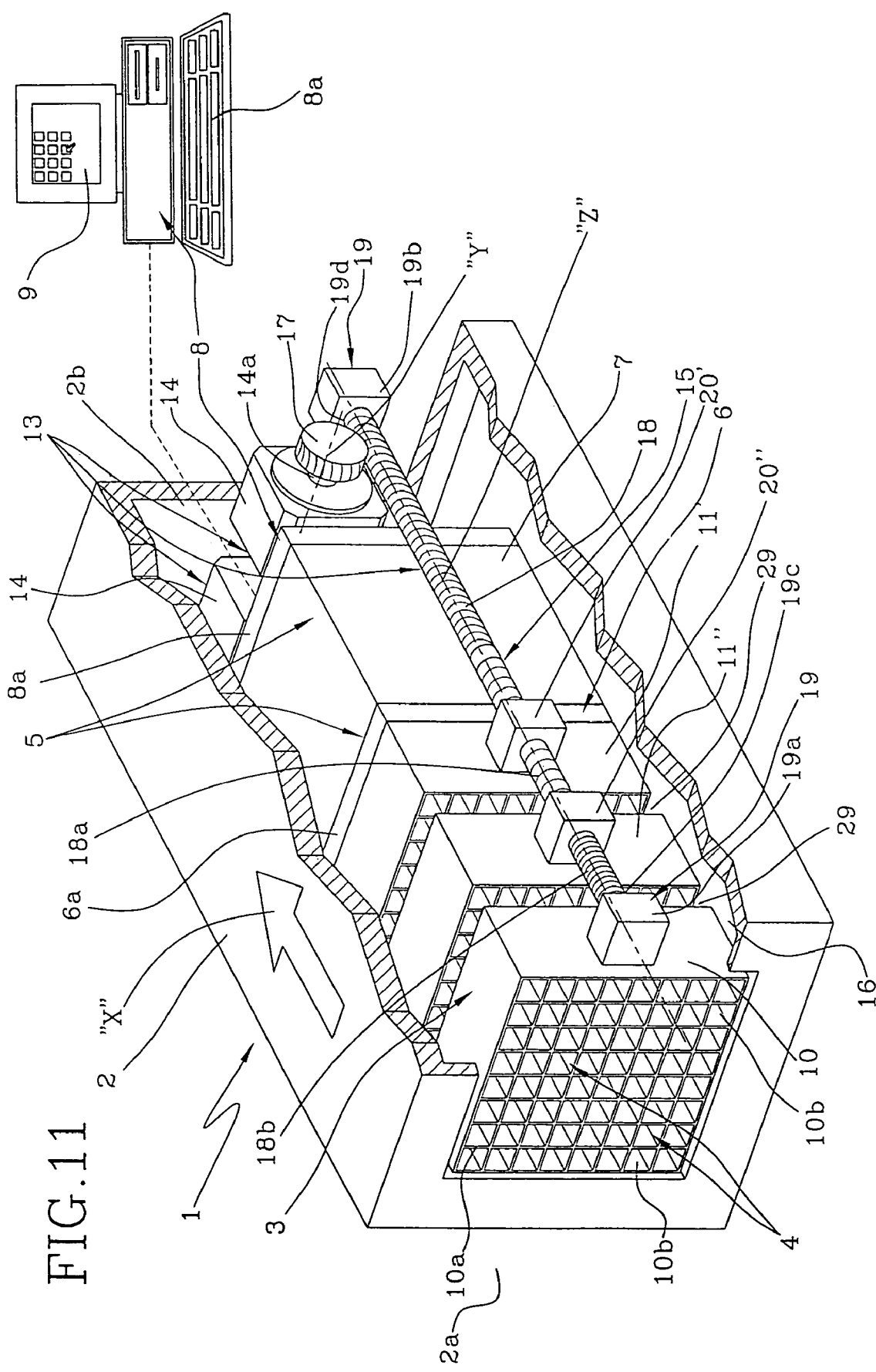
FIG. 11 is a partially interrupted perspective view of the device in accordance with a fourth embodiment of the present invention.
Figure 12:
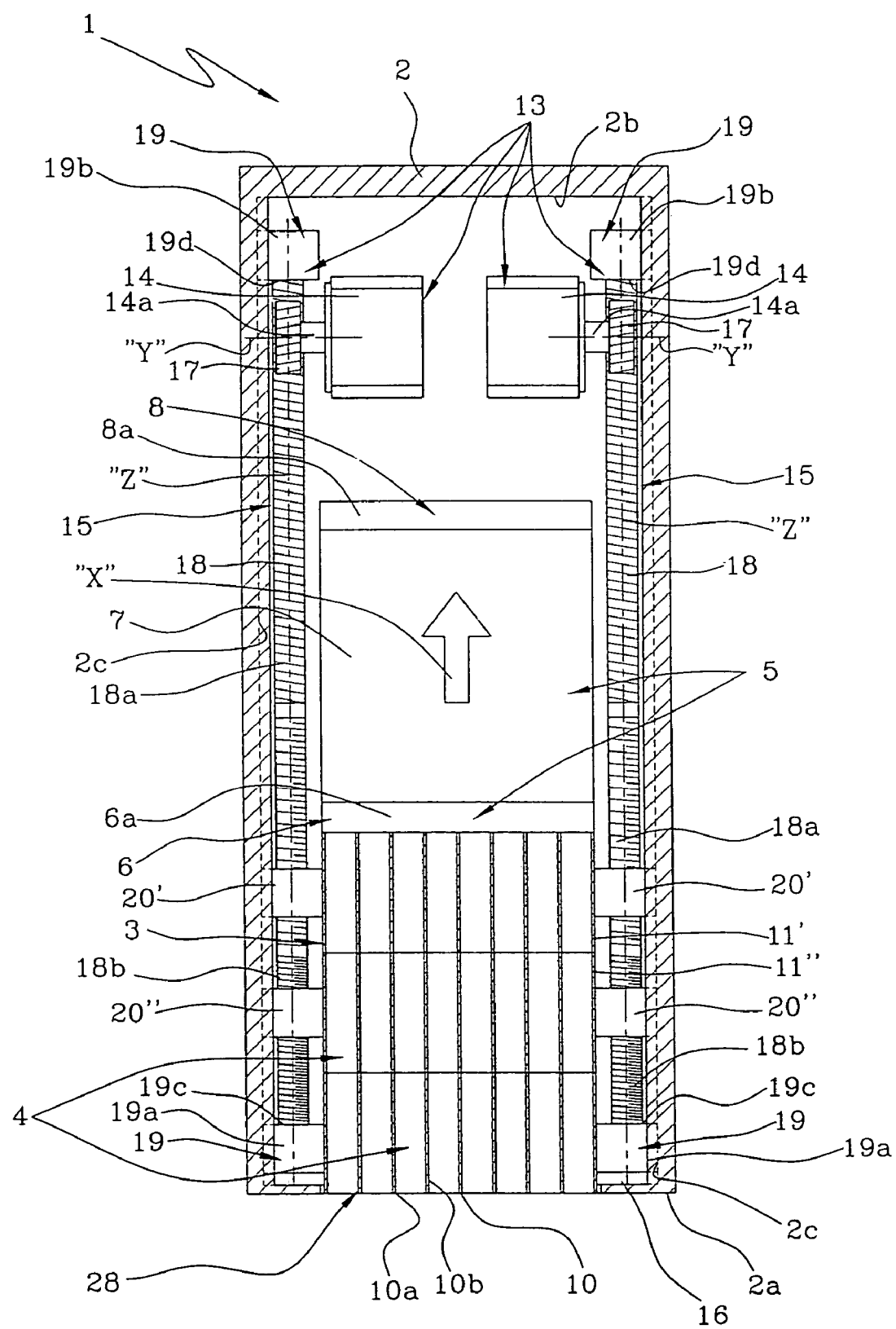
FIG. 12 is a plan section of the device of the previous figure, shown in a first operative position.
Figure 13:
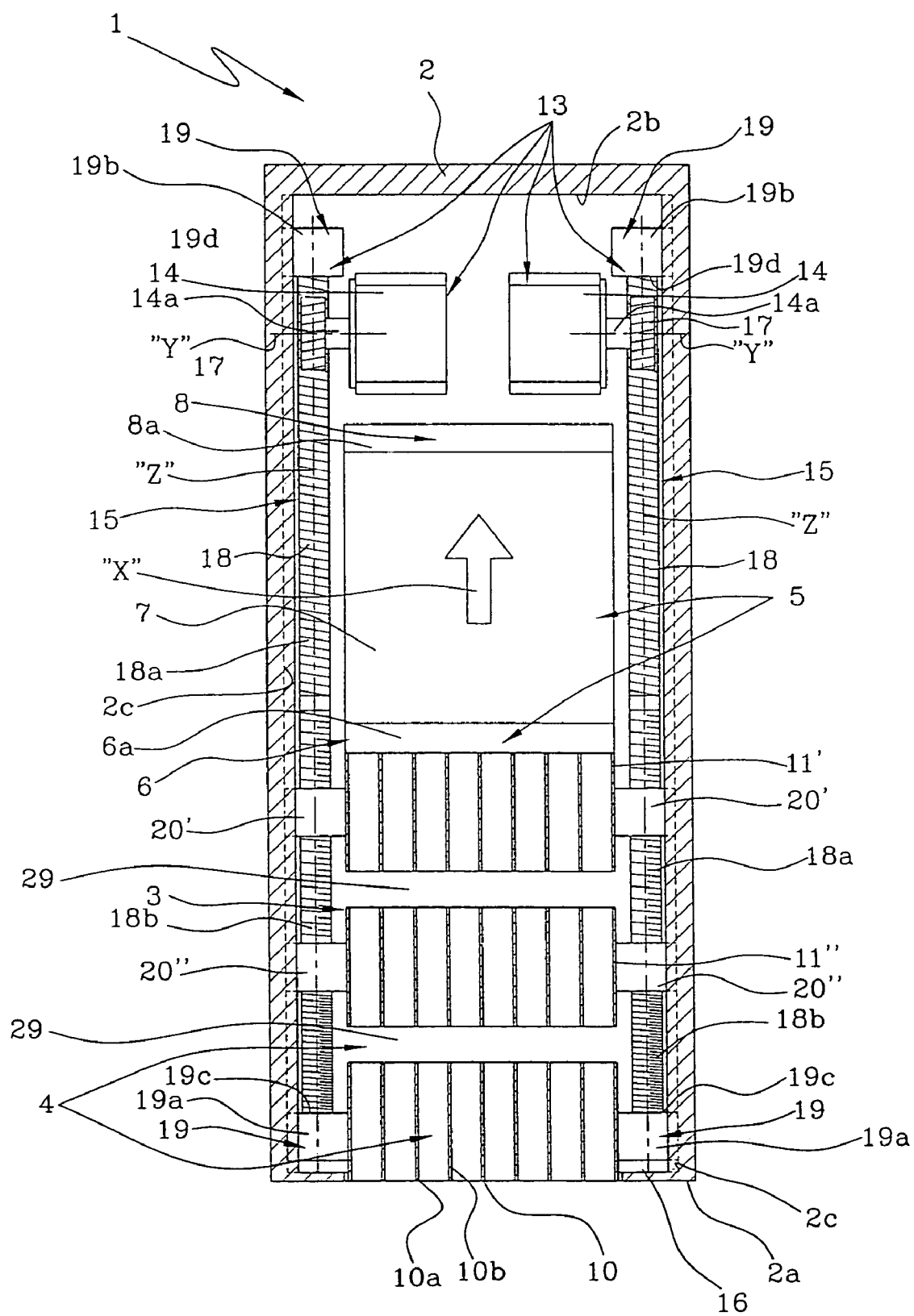
FIG. 13 is a plan section of the device of FIGS. 11 and 12 shown in a second operative position.

In accordance with a fourth embodiment of the present invention, shown in FIGS. 11-13, the collimator 3 differs from the collimators 3 of the other embodiments by the presence of a plurality of mutually equal inner blocks 11', 11b", mutually aligned according to the direction of measurement "X" and interposed between the application block 10 and the measuring member 5.

Similarly to the solutions described above, at least one of the inner blocks 11', 11" is integrally engaged to the measuring member 5 in such a way as to translate together with the member along the direction of measurement "X". Moreover, the inner blocks 11', 11" are movable with respect to one another and with respect to the application block 10 between a condition of contraction (FIG. 12), in which each block 10, 11', 11" is in contact with at least one of the other blocks 10, 11', 11" to define a single block 28, and an expansion condition (FIG. 13), in which each block 10, 11', 11" is distanced from the block 10, 11', 11" and/or the blocks 10, 11', 11" adjacent to define respective interstices 29 whose dimension, measured parallel to the direction of measurement "X" does not exceed 10 mm, in such a way as not to influence negatively the operation of the device 1 and, preferably, it does not exceed 6 mm.

Moreover, the length of each block 10, 11', 11" measured parallel to the direction of measurement "X" is preferably between 2 mm and 10 mm, so that, when the collimator 3 is in the contracted condition (FIG. 12), i.e. in the condition of minimum length, it extends from the measuring member 5 to the application end 2a of the case 2, when instead it is in the expanded condition (FIG. 13), i.e. in the condition of maximum length, its longitudinal development is preferably no smaller than 48 mm.

The expanded condition, characterized by alternating blocks 10, 11', 11" and interstices 29, is managed by the electronic processing unit 8, according to a calculation of the optimized distances to achieve the best result. In any case, it is understood that the interstices 29 must have sufficient longitudinal dimensions to assure collimation effectiveness between a block 10, 11', 11" and the other.

It should also be stressed that the height of each individual block 10, 11', 11" of the collimator is determined as a function of total length and of the number of blocks 10, 11', 11" to be actuated individually.

According to this statement, the equation that allows to determine the maximum length of the collimator is:

$$l = n\,x + (n-1)z$$

where l is the total length of the collimator 3; n is the number of blocks 10, 11a, 11b, 11c of the collimator 3; x is the height of the single block 10, 11a, 11b, 11c; n−1 is the number of empty interstices 29 obtainable between the blocks 10, 11a, 11b, 11c and x is the single distance between the blocks 10, 11a, 11b, 11c.

In a more general formulation, the aforementioned relationship is:

$$l = \sum_{j=1}^{m} n_i x_i + (n-1)_i z_i$$

In case of minimum length, the terms (n−1) z are nil, i.e. the blocks 10, 11a, 11b, 11c lack a separating distance between them.

With reference to FIGS. 11-13, the actuating member 13 of the device 1 has worm screws 18 having, for each inner block 11', 11", at least one portion 18a, 18b with differentiated pitch operatively engaged by a respective actuating cursor 20', 20". Each cursor 20', 20" translates on the respective portion 18a, 18b of the respective worm screw 18 according to different speeds of advance and is fastened to the respective inner block 11', 11" to actuate said block along the direction of measurement "X". Alternatively, in a hypothetical solution not shown in the aforementioned figures, the device 1 may comprise, for each inner block 11', 11" a respective actuating member similar to the actuating members 13, 23 described with reference to the second (FIGS. 4-6) and third embodiment (FIGS. 8-10), i.e. provided with respective electric motors and respective transmission means. Advantageously, said solution allows the independent actuation of each inner block relative to the other blocks.

Figure 14:
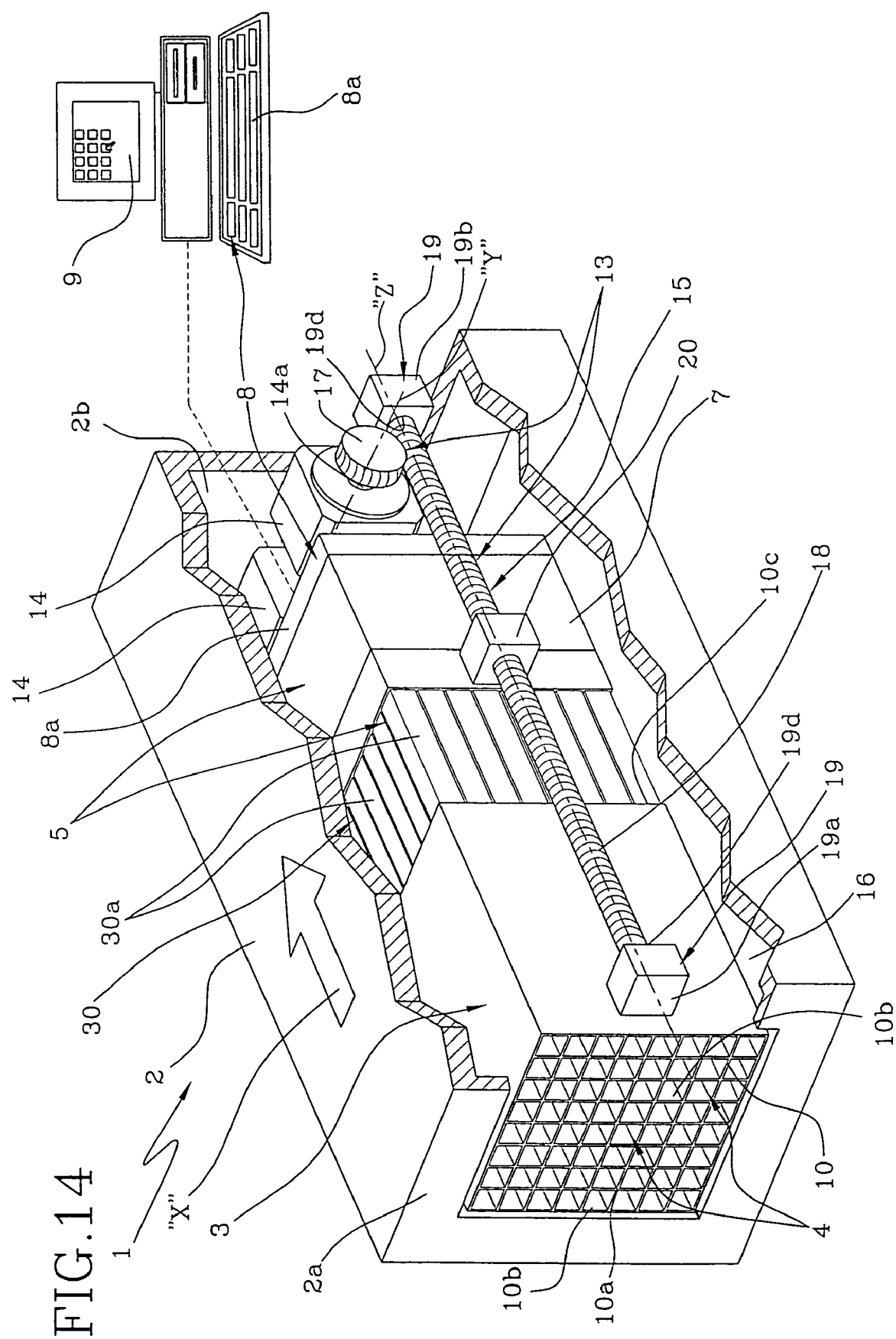
FIG. 14 is a partially interrupted perspective view of the device in accordance with a fifth embodiment of the present invention.

In accordance with a fifth embodiment of the present invention, shown in FIGS. 14-16, the collimator 3 is preferably constituted by a single application block 10 within which the measuring member 5 can slide along the direction of measurement "X". In this situation, the actuating member 13, which has the same elements described with reference to the first embodiment, is directly connected to the measuring member 5 by means of the actuating cursor 20. In this case, the collimator 3 always has the same length, while the distance between the application end 2a of the case 2 and the measuring member 5 is reduced (FIG. 15) and/or increased (FIG. 16) by the actuation of the measuring member itself. In detail, the measuring member 5 is constituted by a plurality of scintillation crystals 6b each having smaller maximum transverse dimensions than the minimum transverse dimensions of the respective collimation channel of the collimator 3 to slide longitudinally inside the collimator 3. The measuring member 5 also comprises linear diffusion means 30 associated to the scintillation crystals 6b of the converter 6 to guide the light radiation coming from said crystals 6b according to a predefined direction to a photosensor 7. In particular, the linear diffusion means 30 comprise a plurality of light guiding elements 30a, each supporting a respective scintillation crystal 6b of the converter 6 and engaged, at the opposite side from said crystals 6b, to the photosensor 7. Preferably, the light guiding elements have transverse dimensions that are equal to the transverse dimensions of the respective scintillation crystals 6b to slide together with them inside the respective collimation channels 4.

The device 1 also has, for each illustrated embodiment, a system of stops and/or end stops (not show for reasons of clarity) capable of arresting the advance of the components in actuation, preventing them from being extracted from the components constituting the guides. In particular, said stops operate, in the case of the embodiments with movable blocks (FIGS. 1-10), between one block and the other and, in the case of the single-block solution (FIG. 14-16), between the latter and the measuring member 5 defining the maximum travel of each movable component.

Figure 17:
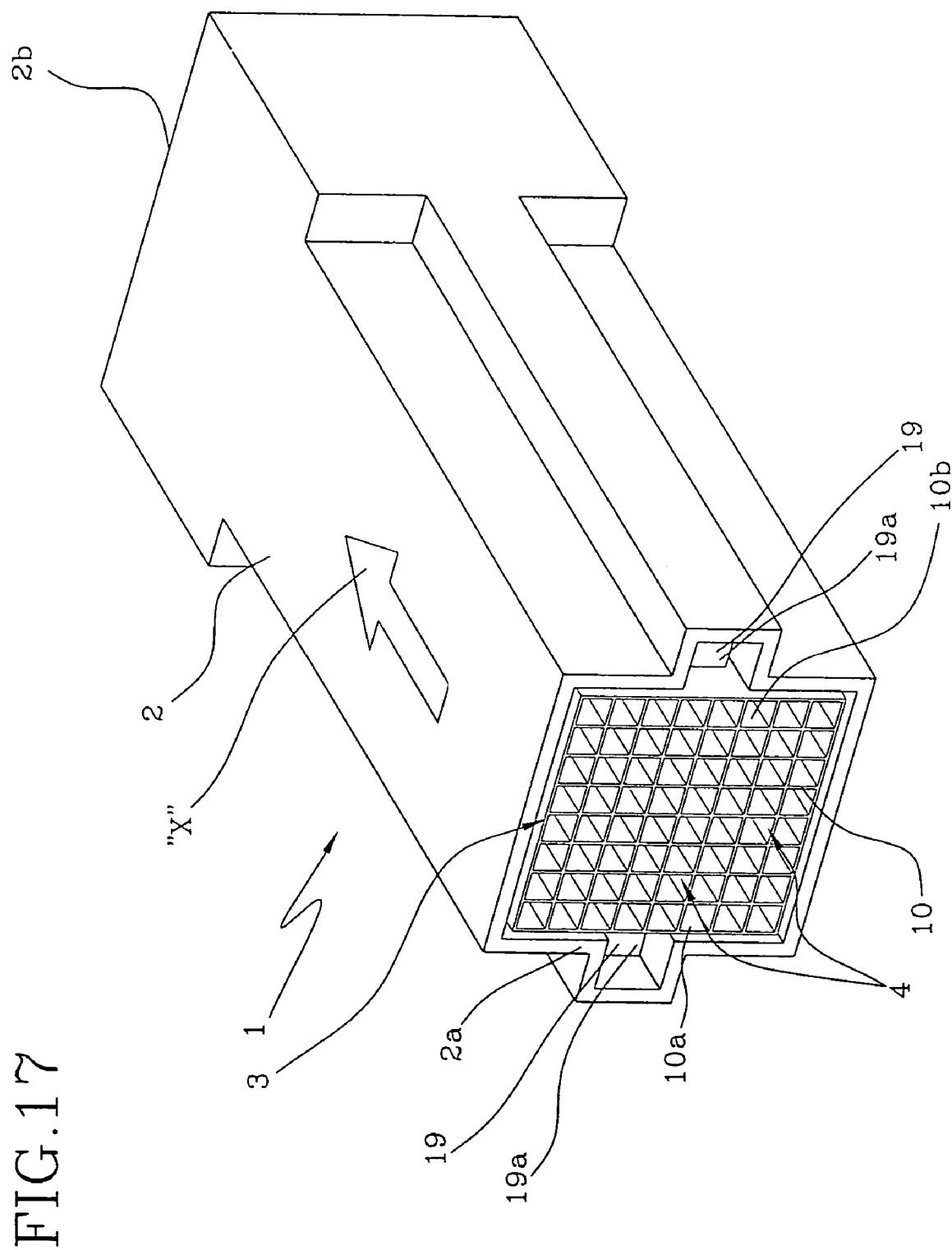
FIG. 17 is a perspective view of the device shown with a different case from that of the previous figures.

In accordance with a sixth embodiment of the present invention, illustrated in FIG. 17, the case of the device develops flush with the collimator 6 and with all components of the actuating organ 13, minimizing the overall mass and size of the device.

The present invention solves the problems noted in the prior art and achieves the proposed object.

First of all, the scintigraphic device 1 according to the present invention enables to perform exams with high spatial resolution, especially on regions of interest located at a depth of about 1 cm.

Moreover, the device 1 described above can be adapted to any kind of exam without requiring the replacement of any component, such as the collimator 3, and without being replaced by a scintigraphic device 1 having different characteristics.

In particular, the scintigraphic device 1 is able to adjust, in manual or automatic mode, the overall length of the collimator 3 electronically managing its actuation along the direction of measurement "X" and its elongation or shortening.

The placement of all the components of the device 1, including those for actuating the blocks of the collimator and/or the measuring member, inside the case 2 provides the device with a compact shape and a limited bulk, necessary for greater convenience of use during the exams.

In addition, the combined use of devices with such characteristics also enables other dedicated applications, e.g. integrating said devices with other diagnostic techniques such as those with ultrasounds, X-rays, magnetic resonance, and so on.

Another advantageous application of the invention pertains to the ability to mount, in a multiple device, sections of the visual field provided with collimators of different height (but also simultaneously of equal or different collimation pitch) allowing a better identification of lesions located at different depth, in terms of lesion/background ratio and contrast measured on the image obtained.

Moreover, the aforesaid device is suitable for use in various sectors other than the medical/diagnostic field, such as astrophysics, in which the single photomultipliers based on the proposed examples are joined to form ample measurement areas, or industrial application, within control systems and non destructive diagnostics.

Obviously, construction details and embodiments may vary widely from what is described purely by way of example herein, without thereby departing from the scope of the present invention as claimed hereafter.

What is claimed is:

1. A scintigraphic device comprising:
  a case open at an application end, said case being coated by a shielding shell;
  a collimator made of a material with high atomic number and high density having a plurality of collimation channels extending substantially parallel with respect to one another and according to a predefined direction of measurement, said collimator being positioned inside said case in such a way as to allow the passage of ionizing radiation directed substantially parallel to the direction of measurement;
  a measuring member positioned inside said case in proximity to said collimator, said measuring member comprising at least one converter able to convert a ionizing radiation coming from a source in exam into at least one light radiation and at least one photosensor to determine the energy and the position of single events;
  at least one electronic processing unit operatively associated to said photosensor to determine the position of an event,
  wherein said collimator and said measuring member are relatively movable between a first position in which the measuring member is positioned at said application end and a second position in which the measuring member is positioned at predetermined distance from said application end, said collimator being extendable and reducible in length.

2. Device as claimed in claim 1, wherein said collimator comprises at least one application block having a substantially square matrix structure positioned at said application end of said case according to a fixed position, said measuring member being movable between the first and the second position along a substantially parallel direction to the direction of measurement.

3. Device as claimed in claim 2, wherein said application block of said collimator has a plurality of collimation conduits developing substantially parallel relative to the direction of measurement and said converter of said measuring member has, for each collimation conduit, a respective scintillation crystal and a respective photosensor, said measuring member engaging, at least with the scintillation crystals, the collimation conduits of said application block when said measuring member is situated in first position.

4. Device as claimed in claim 2, wherein said collimator further comprises at least one inner block positioned at said measuring member between the latter and said application block and at least one intermediate block connected between said application block and said inner block, each of said intermediate and inner blocks having a structure conformed substantially as a square matrix, provided with a plurality of collimation conduits extending substantially parallel relative to the direction of measurement, and aligned to respective collimation conduits of said application block according to the direction of measurement.

5. Device as claimed in claim 4, wherein each of the collimation conduits of said intermediate block has different transverse dimensions from the transverse dimensions of the collimation conduits of said application block and inner block.

6. Device as claimed in claim 4, wherein each of said collimation conduits of said intermediate block has smaller maximum transverse dimensions than the minimum transverse dimensions of the respective collimation conduits at least of said inner block.

7. Device as claimed in claim 6, wherein said intermediate block is integrally engaged to said application block at the opposite side relative to said application end and said inner block is solidly engaged to said measuring member and is movable together with it between the first and the second position, said inner block being operatively engaged to said intermediate block in such a way that the latter is partially inserted in said inner block, when said measuring member is situated in the first position, and placed at a terminal edge of said inner block, when said measuring member is situated in the second position.

8. Device as claimed in claim 6, wherein each of the collimation conduits of said intermediate block has smaller maximum transverse dimensions than the minimum transverse dimensions of the respective collimation conduits of said application block.

9. Device as claimed in claim 8, wherein:
said intermediate block is operatively engaged to said application block at the opposite side from said application end, said intermediate block being movable between a first position, in which it is at least partially inserted within said application block, and a second position, in which said intermediate block is positioned at a terminal edge of said application block;
said inner block is integrally engaged to said measuring member to move together with it between the first and the second position, said inner block being operatively engaged to said intermediate block in such a way that said block is partially inserted in said inner block, when said measuring member is situated in first position, and located at a terminal edge of said inner block, when said measuring member is in second position.

10. Device as claimed in claim 4, wherein each of said collimation conduits of said intermediate block has smaller transverse dimensions than the minimum transverse dimensions of the respective collimation conduits of said application block and greater minimum transverse dimensions than the maximum transverse dimensions of the collimation conduits of said inner block.

11. Device as claimed in claim 10, wherein:
said intermediate block is operatively engaged to said application block at the opposite side with respect to said application end, said intermediate block being movable between a first position, in which it is at least partially inserted within said application block, and a second position, in which said intermediate block is positioned at a terminal edge of said application block;
said inner block is solidly engaged to said measuring member to move together with it between the first and the second position, said inner block being operatively engaged to said intermediate block in such a way as to be partially inserted therein, when said measuring member is situated in first position, and located at a terminal edge of said intermediate, when said measuring member is situated in second position.

12. Device as claimed in claim 4, further comprising at least one actuating member operatively associated to said case to determine the relative actuation between said collimator and measuring member.

13. Device as claimed in claim 12, wherein said actuating member comprises:
at least one motor operatively engaged within said case in proximity to said measuring member;
transmission means operatively interposed between said motor and at least said measuring member, said transmission means developing mainly between said measuring member and said case.

14. Device as claimed in claim 13, wherein said transmission means comprise:
at least one gear wheel with helical teeth keyed on a drive shaft projecting from said motor, said gear wheel rotating integrally with said drive shaft around an axis or rotation substantially perpendicular relative to the direction of measurement;
at least one worm screw developing substantially parallel relative to the direction of measurement, said worm screw being meshed by said gear wheel to rotate around its own longitudinal axis;
at least one actuating cursor operatively engaged to said worm screw at the opposite side relative to said gear wheel to translate thereon along a direction that is substantially parallel to the direction of measurement;
support means engaging said worm screw to sustain it at least between said measuring member and said case, said support means constraining said worm screw so that it is free to rotate around its own longitudinal axis.

15. Device as claimed in claim 14 wherein said actuating cursor is fixed to said measuring member to drive it in rotation between the first and the second position as a result of the operation of said motor.

16. Device as claimed in claim 14, wherein said actuating cursor is fastened to said inner block of said collimator to drive said inner block and said measuring member between the first and the second position as a result of the operation of said motor.

17. Device as claimed in claim 14, wherein said actuating cursor is fastened to said inner block of said collimator to actuate said inner block and said measuring member between the first position and the second position, said device further comprising an auxiliary actuating member operatively interposed between said collimator and said case to actuate said intermediate block between the first and the second position.

18. Device as claimed in claim 17, wherein said auxiliary actuating member comprises:
an auxiliary motor;
auxiliary transmission means operatively interposed between said auxiliary motor and said intermediate block of said collimator.

19. Device as claimed in claim 18, wherein said auxiliary transmission means comprise:
at least one auxiliary gear wheel with helical teeth keyed on an auxiliary drive shaft projecting from said auxiliary motor, said auxiliary gear wheel rotating integrally to said auxiliary drive shaft around an axis of rotation that is substantially perpendicular to the direction of measurement;
at least one auxiliary worm screw developing substantially parallel relative to the direction of measurement, said auxiliary worm screw being meshed by said auxiliary worm gear to rotate around its own longitudinal axis;
at least one auxiliary actuating cursor operatively engaged to said auxiliary worm screw at the opposite part with respect to said auxiliary gear wheel, to translate on said auxiliary worm screw along a direction that is substantially parallel to the direction of measurement, said auxiliary actuating cursor being fastened to said intermediate block of said collimator to actuate said intermediate block between the first and the second position as a result of the operation of said auxiliary motor;

auxiliary support means engaging said auxiliary worm screw to sustain it between said measuring member and said case, said auxiliary support means constraining said auxiliary worm screw in such a way that it is free to rotate only around its own longitudinal axis.

20. Device as claimed in claim 14, wherein said worm screw has two consecutive portions with differentiated pitch operatively engaged respectively by said actuating cursor and by an auxiliary actuating cursor of said transmission means, said actuating cursor and auxiliary actuating cursor translating on the respective portions of said worm screw according to differentiated speeds of advance and being fastened respectively to said inner block and intermediate block of said collimator to move respectively said inner block together with said measuring member between the first and the second position and said intermediate block between the first and the second position as a result of the operation of said motor.

21. Device as claimed in claim 14, wherein for each inner block of said collimator, said worm screw has a respective portion with differentiated pitch operatively engaged by a respective actuating cursor, each actuating cursor translating on the respective portion of said worm screw according to a predetermined speed of advance and being fastened to the respective inner block to actuate it along said direction of measurement.

22. Device as claimed in claim 14, wherein for each inner block there is a respective actuating member able to be operated independently of the other actuating members.

23. Device as claimed in claim 2, wherein said collimator also has a plurality of inner blocks each having a structured that is substantially conformed as a square matrix and provided with a plurality of collimation conduits extending substantially parallel to the direction of measurement, the inner blocks being interposed between said measuring member and said application block and being aligned along the direction of measurement in such a way that the collimation conduits of each inner block are aligned with the collimation conduits of the other blocks.

24. Device as claimed in claim 23, wherein at least one of said inner blocks is integrally engaged to said measuring member to move together therewith between the first and the second position.

25. Device as claimed in claim 23, wherein said inner blocks are movable relative to one another and relative to the application block between a contracted condition, in which each block is in contact with at least one of said blocks to define a single block, and an expanded condition, in which each block is distanced from the block and/or the adjacent blocks to define corresponding interstices having predefined dimensions.

26. Scintigraphic device comprising:
a case open at an application end, said case being coated by a shielding shell;
a collimator made of a material with high atomic number and high density having a plurality of collimation channels extending substantially parallel with respect to one another and according to a predefined direction of measurement, said collimator being positioned inside said case in such a way as to allow the passage of ionizing radiation directed substantially parallel to the direction of measurement, said collimator being extendable and reducible in length;
a measuring member positioned inside said case in proximity to said collimator, said measuring member comprising at least one converter able to convert a ionizing radiation coming from a source in exam into at least one light radiation and at least one photosensor to determine the energy and the position of single events, said measuring member also comprising linear diffusion means associated to guide the light radiation coming from the scintigraphic device;
at least one electronic processing unit operatively associated to said photosensor to determine the position of an event,
wherein:
said collimator comprises, for collimation channel, a respective scintillation crystal;
said linear diffusion means comprise, for each collimation channel, a respective light guiding element supporting, on one side, the respective scintillation crystal of said converter and engaged, at the other side, to said photosensor, said measuring member being movable relative to said collimator between a first position, in which the scintillation crystals of said converter are situated at said application end of said case, and a second position in which the scintillation crystals of said converter are positioned at a predetermined distance from said application end.

27. Device as claimed in claim 26, wherein said scintillation crystals and said light guiding elements have smaller maximum transverse dimensions than the minimum transverse dimensions of the collimation channels so that both the scintillation crystals and the light guiding elements are free to translate inside the respective collimation channels between the first and the second position.

28. A scintigraphic device comprising:
a case open at an application end, said case being coated by a shielding shell;
a collimator made of a material with high atomic number and high density having a plurality of collimation channels extending substantially parallel with respect to one another and according to a predefined direction of measurement, said collimator being positioned inside said case in such a way as to allow the passage of ionizing radiation directed substantially parallel to the direction of measurement;
a measuring member positioned inside said case in proximity to said collimator, said measuring member comprising at least one converter able to convert an ionizing radiation coming from a source in exam into at least one light radiation and at least one photosensor to determine the energy and the position of single events;
at least one electronic processing unit operatively associated to said photosensor to determine the position of an event,
wherein said collimator and said measuring member are relatively movable between a first position in which the measuring member is positioned at said application end and a second position in which the measuring member is positioned at predetermined distance from said application end, said collimator comprising at least one inner block positioned at said measuring member between the latter and said application block and at least one intermediate block connected between said application block and said inner block, each of said intermediate and inner blocks having a structure conformed substantially as a square matrix, provided with a plurality of collimation conduits extending substantially parallel relative to the direction of measurement, and aligned to respective collimation conduits of said application block according to the direction of measurement.

* * * * *